(12) United States Patent
Tsai

(10) Patent No.: US 7,037,668 B2
(45) Date of Patent: May 2, 2006

(54) METHODS FOR THE TREATMENT AND DIAGNOSIS OF TUMORIGENIC AND ANGIOGENIC DISORDERS USING 32616

(75) Inventor: Fong-Ying Tsai, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 593 days.

(21) Appl. No.: 10/283,013

(22) Filed: Oct. 29, 2002

(65) Prior Publication Data

US 2003/0087872 A1    May 8, 2003

Related U.S. Application Data

(60) Provisional application No. 60/334,996, filed on Oct. 31, 2001.

(51) Int. Cl.
*G01N 33/574*  (2006.01)
*G01N 33/567*  (2006.01)
*G01N 33/53*   (2006.01)
*C12Q 1/34*    (2006.01)

(52) U.S. Cl. .................. 435/7.23; 435/7.1; 435/7.21; 435/18

(58) Field of Classification Search ............ None
See application file for complete search history.

(56) References Cited

U.S. PATENT DOCUMENTS 6,590,075 B1 *   7/2003   Ruben et al. ............... 530/350

FOREIGN PATENT DOCUMENTS

| EP | 1 067 182 A2 | 7/2000 |
|---|---|---|
| WO | WO 00/05367 A2 | 2/2000 |
| WO | WO 01/57190 A2 | 8/2001 |

OTHER PUBLICATIONS

Tang, Y.T., et al., "Nucleic Acids Encoding Polypeptides with Cytokine-Like Activities, Useful in Diagnosis and Gene Therapy," Nov. 6, 2001, (sequence), EMBL Database [online], Hinxton, Cambridge, U.K., European Bioinformatics Institute, [retrieved on Oct. 20, 2004]. Retrieved from the Internet: URL: http://www.ebi.ac.uk/embl/>. EMBL Accession No. AAM79326.

Kato, S., et al., "Novel Human Proteins Having Hydrophobic Domains Useful for Treating Osteoporosis, alzheimer's Disease, Parkinson's Disease, Asthma, Multiple Sclerosis, Rheumatoid Arthritis, Cancer, Anemia, and Stroke," Jun. 12, 2000, (sequence), EMBL Database [online], Hinxton, Cambridge, U.K., European Bioinformatics Institute, [retrieved on Oct. 20, 2004]. Retrieved from the Internet: URL: http://www.ebi.ac.uk/embl/>. EMBL Accession No. AAY94860.

* cited by examiner

Primary Examiner—Sean McGarry
Assistant Examiner—Louis Wollenberger
(74) Attorney, Agent, or Firm—Millennium Pharmaceuticals, Inc.

(57) ABSTRACT

The present invention relates to methods and compositions for the treatment and diagnosis of tumorigenic and/or angiogenic disorders, including, but not limited to, lung tumors, breast tumors, ovary tumors, colon tumors, hemangioma, and metastatic and angiogenic tumors. The invention further provides methods for identifying a compound capable of treating a tumorigenic and/or angiogenic disorder or modulating tumorigenesis and/or angiogenesis. The invention also provides methods for modulating tumorigenesis and/or angiogenesis, e.g., modulating tumorigenesis and/or angiogenesis in a subject. In addition, the invention provides a method for treating a subject having a tumorigenic and/or angiogenic disorder characterized by aberrant 32616 polypeptide activity or aberrant 32616 nucleic acid expression.

6 Claims, 7 Drawing Sheets

> Fbh32616pub - Import - vector trimmed
GCACCCACCCGTCCGGGAAGAACAAGCGCTCCCGAGGCCGCGGGAGCCTGCAGAGAGGAC
AGCCGGCCTGCGCCGGGACATGCGGCCCCAGGAGCTCCCCAGGCTCGCGTTCCCGTTGCT
GCTGTTGCTGTTGCTGCTGCTGCCGCCGCCGCCGTGCCCTGCCCACAGCGCCACGCGCTT
CGACCCCACCTGGGAGTCCCTGGACGCCCGCCAGCTGCCCGCGTGGTTTGACCAGGCCAA
GTTCGGCATCTTCATCCACTGGGGAGTGTTTTCCGTGCCCAGCTTCGGTAGCGAGTGGTT
CTGGTGGTATTGGCAAAAGGAAAAGATACCGAAGTATGTGGAATTTATGAAAGATAATTA
CCCTCCTAGTTTCAAATATGAAGATTTTGGACCACTATTTACAGCAAAATTTTTTAATGC
CAACCAGTGGGCAGATATTTTTCAGGCCTCTGGTGCCAAATACATTGTCTTAACTTCCAA
ACATCATGAAGGCTTTACCTTGTGGGGCCAGAATATTCGTGGAACTGGAATGCCATAGA
TGAGGGGCCCAAGAGGGACATTGTCAAGGAACTTGAGGTAGCCATTAGGAACAGAACTGA
CCTGCGTTTTGGACTGTACTATTCCCTTTTTGAATGGTTTCATCCGCTCTTCCTTGAGGA
TGAATCCAGTTCATTCCATAAGCGGCAATTTCCAGTTTCTAAGACATTGCCAGAGCTCTA
TGAGTTAGTGAACAACTATCAGCCTGAGGTTCTGTGGTCGGATGGTGACGGAGGAGCACC
GGATCAATACTGGAACAGCACAGGCTTCTTGGCCTGGTTATATAATGAAAGCCCAGTTCG
GGGCACAGTAGTCACCAATGATCGTTGGGGAGCTGGTAGCATCTGTAAGCATGGTGGCTT
CTATACCTGCAGTGATCGTTATAACCCAGGACATCTTTTGCCACATAAATGGGAAAACTG
CATGACAATAGACAAACTGTCCTGGGGCTATAGGAGGGAAGCTGGAATCTCTGACTATCT
TACAATTGAAGAATTGGTGAAGCAACTTGTAGAGACAGTTTCATGTGGAGGAAATCTTTT
GATGAATATTGGGCCCACACTAGATGGCACCATTTCTGTAGTTTTTGAGGAGCGACTGAG
GCAAATGGGGTCCTGGCTAAAAGTCAATGGAGAAGCTATTTATGAAACCCATACCTGGCG
ATCCCAGAATGACACTGTCACCCCAGATGTGTGGTACACATCCAAGCCTTAAAGAAAAAT
TAGTCTATGCCATTTTTCTTAAATGGCCCACATCAGGACAGCTGTTCCTTGGCCATCCCA
AAGCTATTCTGGGGCAACAGAGGTGAAACTACTGGGCCATGACAGCCACTTAACTGGA
TTTCTTTGGAGCAAAATGGCATTATGGTAGAACTGCCACAGCTAACCATTCATCAGATGC
CGTGTAAATGGGGCTGGGCTCTAGCCCTAACTAATGTGATCTAAAGTGCAGCAGAGTGGC
TGATGCTGCAAGTTATGTCTAAGGCTAGGAACTATCAGGTGTCTATAATTGTAGCACATG
GAGAAAGCAAATGTAAAACTGGATAAGAAAATTATTTTGGCAGTTCAGCCCTTTCCCTTT
TTCCCACTAAATTTTTTCTTAAATTACCCATGTAACCATTTTAACTCTCCAGTGCACTTT
GCCATTAAAGTCTCTTCACATTGAAATGTT

FIGURE 1A

```
>32616 protein
MRPQELPRLAFPLLLLLLLLLPPPPCPAHSATRFDPTWESLDARQLPAWFDQAKFGIFIHWGVFSVPSFGSEWFWWYWQ
KEKIPKYVEFMKDNYPPSFKYEDFGPLFTAKFFNANQWADIFQASGAKYIVLTSKHHEGFTLWGPEYSWNWNAIDEGPK
RDIVKELEVAIRNRTDLRFGLYYSLFEWFHPLFLEDESSSFHKRQFPVSKTLPELYELVNNYQPEVLWSDGDGGAPDQY
WNSTGFLAWLYNESPVRGTVVTNDRWGAGSICKHGGFYTCSDRYNPGHLLPHKWENCMTIDKLSWGYRREAGISDYLTI
EELVKQLVETVSCGGNLLMNIGPTLDGTISVVFEERLRQMGSWLKVNGEAIYETHTWRSQNDTVTPDVWYTSKP.
```

FIGURE 1B

SEQUENCE LISTING

<160> NUMBER OF SEQ ID NOS: 3

<210> SEQ ID NO 1
<211> LENGTH: 1710
<212> TYPE: DNA
<213> ORGANISM: Homo sapien

<400> SEQUENCE: 1

```
gcacccaccc gtccgggaag aacaagcgct cccgaggccg cgggagcctg cagagaggac      60
agccggcctg cgccgggaca tgcggcccca ggagctcccc aggctcgcgt tcccgttgct     120
gctgttgctg ttgctgctgc tgccgccgcc gccgtgccct gcccacagcg ccacgcgctt     180
cgaccccacc tgggagtccc tggacgcccg ccagctgccc gcgtggtttg accaggccaa     240
gttcggcatc ttcatccact ggggagtgtt ttccgtgccc agcttcggta gcgagtggtt     300
ctggtggtat tggcaaaagg aaaagatacc gaagtatgtg gaatttatga agataatta     360 ccctcctagt ttcaaatatg aagattttgg accactattt acagcaaaat ttttttaatgc     420 caaccagtgg gcagatattt ttcaggcctc tggtgccaaa tacattgtct taacttccaa     480
acatcatgaa ggctttacct tgtggggggcc agaatattcg tggaactgga atgccataga     540 tgagggccc aagagggaca ttgtcaagga acttgaggta gccattagga acagaactga     600
cctgcgtttt ggactgtact attcccttt tgaatggttt catccgctct tccttgagga     660
tgaatccagt tcattccata agcggcaatt tccagttct aagacattgc cagagctcta     720
tgagttagtg aacaactatc agcctgaggt tctgtggtcg gatggtgacg gaggagcacc     780
ggatcaatac tggaacagca caggcttctt ggcctggtta tataatgaaa gcccagttcg     840
gggcacagta gtcaccaatg atcgttgggg agctggtagc atctgtaagc atggtggctt     900
ctatacctgc agtgatcgtt ataacccagg acatctttg ccacataaat gggaaaactg     960
catgacaata gacaaactgt cctggggcta taggagggaa gctggaatct ctgactatct    1020
tacaattgaa gaattggtga agcaacttgt agagacagtt tcatgtggag gaaatctttt    1080
gatgaatatt gggcccacac tagatggcac catttctgta gtttttgagg agcgactgag    1140
gcaaatgggg tcctggctaa aagtcaatgg agaagctatt tatgaaaccc atacctggcg    1200
atcccagaat gacactgtca ccccagatgt gtggtacaca tccaagcctt aaagaaaaat    1260
tagtctatgc catttttctt aaatggccca catcaggaca gctgttcctt ggccatccca    1320
aagctattct gggggcaaca gaggtgaaac tactgggcca tggacagcca cttaactgga    1380
tttctttgga gcaaaatggc attatggtag aactgccaca gctaaccatt catcagatgc    1440
cgtgtaaatg gggctgggct ctagccctaa ctaatgtgat ctaaagtgca gcagagtggc    1500
```

-continued

```
tgatgctgca agttatgtct aaggctagga actatcaggt gtctataatt gtagcacatg    1560
gagaaagcaa atgtaaaact ggataagaaa attattttgg cagttcagcc ctttcccttt    1620
ttcccactaa attttttctt aaattaccca tgtaaccatt ttaactctcc agtgcacttt    1680
gccattaaag tctcttcaca ttgaaatgtt                                     1710
```

<210> SEQ ID NO 2
<211> LENGTH: 390
<212> TYPE: PRT
<213> ORGANISM: Homo sapien

<400> SEQUENCE: 2

```
Met Arg Pro Gln Glu Leu Pro Arg Leu Ala Phe Pro Leu Leu Leu Leu
 1               5                  10                  15

Leu Leu Leu Leu Pro Pro Pro Cys Pro Ala His Ser Ala Thr
            20                  25                  30

Arg Phe Asp Pro Thr Trp Glu Ser Leu Asp Ala Arg Gln Leu Pro Ala
            35                  40                  45

Trp Phe Asp Gln Ala Lys Phe Gly Ile Phe Ile His Trp Gly Val Phe
    50                  55                  60

Ser Val Pro Ser Phe Gly Ser Glu Trp Phe Trp Tyr Trp Gln Lys
65                  70                  75                  80

Glu Lys Ile Pro Lys Tyr Val Glu Phe Met Lys Asp Asn Tyr Pro Pro
                85                  90                  95

Ser Phe Lys Tyr Glu Asp Phe Gly Pro Leu Phe Thr Ala Lys Phe Phe
            100                 105                 110

Asn Ala Asn Gln Trp Ala Asp Ile Phe Gln Ala Ser Gly Ala Lys Tyr
        115                 120                 125

Ile Val Leu Thr Ser Lys His His Glu Gly Phe Thr Leu Trp Gly Pro
    130                 135                 140

Glu Tyr Ser Trp Asn Trp Asn Ala Ile Asp Glu Gly Pro Lys Arg Asp
145                 150                 155                 160

Ile Val Lys Glu Leu Glu Val Ala Ile Arg Asn Arg Thr Asp Leu Arg
                165                 170                 175

Phe Gly Leu Tyr Tyr Ser Leu Phe Glu Trp Phe His Pro Leu Phe Leu
            180                 185                 190

Glu Asp Glu Ser Ser Phe His Lys Arg Gln Phe Pro Val Ser Lys
        195                 200                 205

Thr Leu Pro Glu Leu Tyr Glu Leu Val Asn Asn Tyr Gln Pro Glu Val
    210                 215                 220

Leu Trp Ser Asp Gly Asp Gly Gly Ala Pro Asp Gln Tyr Trp Asn Ser
225                 230                 235                 240

Thr Gly Phe Leu Ala Trp Leu Tyr Asn Glu Ser Pro Val Arg Gly Thr
                245                 250                 255

Val Val Thr Asn Asp Arg Trp Gly Ala Gly Ser Ile Cys Lys His Gly
            260                 265                 270

Gly Phe Tyr Thr Cys Ser Asp Arg Tyr Asn Pro Gly His Leu Leu Pro
        275                 280                 285

His Lys Trp Glu Asn Cys Met Thr Ile Asp Lys Leu Ser Trp Gly Tyr
    290                 295                 300

Arg Arg Glu Ala Gly Ile Ser Asp Tyr Leu Thr Ile Glu Glu Leu Val
305                 310                 315                 320

Lys Gln Leu Val Glu Thr Val Ser Cys Gly Gly Asn Leu Leu Met Asn
                325                 330                 335
```

```
Ile Gly Pro Thr Leu Asp Gly Thr Ile Ser Val Val Phe Glu Glu Arg
                340                 345                 350

Leu Arg Gln Met Gly Ser Trp Leu Lys Val Asn Gly Glu Ala Ile Tyr
            355                 360                 365

Glu Thr His Thr Trp Arg Ser Gln Asn Asp Thr Val Thr Pro Asp Val
        370                 375                 380

Trp Tyr Thr Ser Lys Pro
385                 390

<210> SEQ ID NO 3
<211> LENGTH: 1710
<212> TYPE: DNA
<213> ORGANISM: Homo sapien
<220> FEATURE:
<221> NAME/KEY: CDS
<222> LOCATION: (80)...(1252)

<400> SEQUENCE: 3
gcacccaccc gtccgggaag aacaagcgct cccgaggccg cgggagcctg cagagaggac      60
agccggcctg cgccgggac atg cgg ccc cag gag ctc ccc agg ctc gcg ttc     112
                    Met Arg Pro Gln Glu Leu Pro Arg Leu Ala Phe
                      1               5                    10 ccg ttg ctg ctg ttg ctg ttg ctg ctg ccg ccg ccg ccg tgc cct           160
Pro Leu Leu Leu Leu Leu Leu Leu Leu Pro Pro Pro Pro Cys Pro
                15                  20                  25 gcc cac agc gcc acg cgc ttc gac ccc acc tgg gag tcc ctg gac gcc     208
Ala His Ser Ala Thr Arg Phe Asp Pro Thr Trp Glu Ser Leu Asp Ala
            30                  35                  40 cgc cag ctg ccc gcg tgg ttt gac cag gcc aag ttc ggc atc ttc atc     256
Arg Gln Leu Pro Ala Trp Phe Asp Gln Ala Lys Phe Gly Ile Phe Ile
    45                  50                  55 cac tgg gga gtg ttt tcc gtg ccc agc ttc ggt agc gag tgg ttc tgg     304
His Trp Gly Val Phe Ser Val Pro Ser Phe Gly Ser Glu Trp Phe Trp
 60                  65                  70                  75 tgg tat tgg caa aag gaa aag ata ccg aag tat gtg gaa ttt atg aaa     352
Trp Tyr Trp Gln Lys Glu Lys Ile Pro Lys Tyr Val Glu Phe Met Lys
                 80                  85                  90 gat aat tac cct cct agt ttc aaa tat gaa gat ttt gga cca cta ttt     400
Asp Asn Tyr Pro Pro Ser Phe Lys Tyr Glu Asp Phe Gly Pro Leu Phe
             95                 100                 105 aca gca aaa ttt ttt aat gcc aac cag tgg gca gat att ttt cag gcc     448
Thr Ala Lys Phe Phe Asn Ala Asn Gln Trp Ala Asp Ile Phe Gln Ala
        110                 115                 120 tct ggt gcc aaa tac att gtc tta act tcc aaa cat cat gaa ggc ttt     496
Ser Gly Ala Lys Tyr Ile Val Leu Thr Ser Lys His His Glu Gly Phe
    125                 130                 135 acc ttg tgg ggg cca gaa tat tcg tgg aac tgg aat gcc ata gat gag     544
Thr Leu Trp Gly Pro Glu Tyr Ser Trp Asn Trp Asn Ala Ile Asp Glu
140                 145                 150                 155 ggg ccc aag agg gac att gtc aag gaa ctt gag gta gcc att agg aac     592
Gly Pro Lys Arg Asp Ile Val Lys Glu Leu Glu Val Ala Ile Arg Asn
                160                 165                 170 aga act gac ctg cgt ttt gga ctg tac tat tcc ctt ttt gaa tgg ttt     640
Arg Thr Asp Leu Arg Phe Gly Leu Tyr Tyr Ser Leu Phe Glu Trp Phe
            175                 180                 185 cat ccg ctc ttc ctt gag gat gaa tcc agt tca ttc cat aag cgg caa     688
His Pro Leu Phe Leu Glu Asp Glu Ser Ser Ser Phe His Lys Arg Gln
        190                 195                 200
```

```
                                                                    -continued ttt cca gtt tct aag aca ttg cca gag ctc tat gag tta gtg aac aac      736
Phe Pro Val Ser Lys Thr Leu Pro Glu Leu Tyr Glu Leu Val Asn Asn
    205                 210                 215 tat cag cct gag gtt ctg tgg tcg gat ggt gac gga gga gca ccg gat      784
Tyr Gln Pro Glu Val Leu Trp Ser Asp Gly Asp Gly Gly Ala Pro Asp
220                 225                 230                 235 caa tac tgg aac agc aca ggc ttc ttg gcc tgg tta tat aat gaa agc      832
Gln Tyr Trp Asn Ser Thr Gly Phe Leu Ala Trp Leu Tyr Asn Glu Ser
                240                 245                 250 cca gtt cgg ggc aca gta gtc acc aat gat cgt tgg gga gct ggt agc      880
Pro Val Arg Gly Thr Val Val Thr Asn Asp Arg Trp Gly Ala Gly Ser
            255                 260                 265 atc tgt aag cat ggt ggc ttc tat acc tgc agt gat cgt tat aac cca      928
Ile Cys Lys His Gly Gly Phe Tyr Thr Cys Ser Asp Arg Tyr Asn Pro
        270                 275                 280 gga cat ctt ttg cca cat aaa tgg gaa aac tgc atg aca ata gac aaa      976
Gly His Leu Leu Pro His Lys Trp Glu Asn Cys Met Thr Ile Asp Lys
    285                 290                 295 ctg tcc tgg ggc tat agg agg gaa gct gga atc tct gac tat ctt aca     1024
Leu Ser Trp Gly Tyr Arg Arg Glu Ala Gly Ile Ser Asp Tyr Leu Thr
300                 305                 310                 315 att gaa gaa ttg gtg aag caa ctt gta gag aca gtt tca tgt gga gga     1072
Ile Glu Glu Leu Val Lys Gln Leu Val Glu Thr Val Ser Cys Gly Gly
                320                 325                 330 aat ctt ttg atg aat att ggg ccc aca cta gat ggc acc att tct gta     1120
Asn Leu Leu Met Asn Ile Gly Pro Thr Leu Asp Gly Thr Ile Ser Val
                335                 340                 345 gtt ttt gag gag cga ctg agg caa atg ggg tcc tgg cta aaa gtc aat     1168
Val Phe Glu Glu Arg Leu Arg Gln Met Gly Ser Trp Leu Lys Val Asn
            350                 355                 360 gga gaa gct att tat gaa acc cat acc tgg cga tcc cag aat gac act     1216
Gly Glu Ala Ile Tyr Glu Thr His Thr Trp Arg Ser Gln Asn Asp Thr
        365                 370                 375 gtc acc cca gat gtg tgg tac aca tcc aag cct taa agaaaatta           1262
Val Thr Pro Asp Val Trp Tyr Thr Ser Lys Pro *
380                 385                 390 gtctatgcca ttttctttaa atggcccaca tcaggacagc tgttccttgg ccatcccaaa   1322
gctattctgg gggcaacaga ggtgaaacta ctgggccatg acagccact taactggatt    1382 tctttggagc aaaatggcat tatggtagaa ctgccacagc taaccattca tcagatgccg   1442
tgtaaatggg gctgggctct agccctaact aatgtgatct aaagtgcagc agagtggctg   1502
atgctgcaag ttatgtctaa ggctaggaac tatcaggtgt ctataattgt agcacatgga   1562
gaaagcaaat gtaaaactgg ataagaaaat tattttggca gttcagcct ttccctttt     1622 cccactaaat tttttcttaa attacccatg taaccatttt aactctccag tgcactttgc   1682
cattaaagtc tcttcacatt gaaatgtt                                      1710
```

METHODS FOR THE TREATMENT AND DIAGNOSIS OF TUMORIGENIC AND ANGIOGENIC DISORDERS USING 32616

Portions of this application are contained on a compact disc, which is herein incorporated by reference.

This application claims priority to U.S. provisional application No. 60/334,996, filed Oct. 31, 2001, the entire contents of which are herein incorporated by reference.

Cancer is the second leading cause of death in the United States, after heart disease (Boring, et al., (1993) *CA Cancer J. Clin.* 43:7). Cancer is characterized primarily by an increase in the number of abnormal, or neoplastic, cells derived from a normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

The switch in tumors from the quiescent state to malignancy is signaled by the commencement of the angiogenesis process. Tumors need an extensive network of capillaries to provide nutrients and oxygen. Solid tumors will not grow beyond 2 millimeters without new blood vessels. Malignancy and invasion are angiogenesis dependent. The concept behind angiogenesis is simple: tumors must build new blood vessels to enhance the delivery of vital nutrients that allow them to grow and spread. As with many facets of cancer, angiogenesis plays a role in normal cellular growth and maturation. Capillaries grow when and where they are needed—during the development of a fetus, for example—and don't usually grow when they are not required. Normal tissues have an intricate system which controls when to turn angiogenesis on or off. Tumor cells are able to override this system and turn on the growth of blood vessels, which in turn allow the tumor to grow from a bundle of a few mutated cells into a tumor mass, that has the capability to metastasize and kill.

Colorectal cancer is among the most common cancers affecting the western world. An estimated 129,400 new cases of colorectal cancer occurred in the United States in 1999 (Rudy, et al. (2000) *Am Fam Physician* 61(6):1759–70, 1773–4). By the age of 70 years, at least 50% of the Western population will develop some form of colorectal tumor, including early benign polyps and invasive adenocarcinomas. It is estimated that approximately 10% of the benign polypoid lesions will progress to invasive carcinoma (Fahy et al. (1998) *Surg Oncol* 7(3–4): 115–23). Colorectal cancer arises from a precursor lesion, the adenomatous polyp, which forms in a field of epithelial cell hyperproliferation and crypt dysplasia. Progression from this precursor lesion to colorectal cancer is a multistep process (Winawer (1999) *Am J Med* 106(1A):3S–6S).

Ovarian cancer is the second most common cancer of the female reproductive organs and the fourth leading cause of cancer deaths among American women. There are three main types of ovarian tumors: epithelial tumors, germ cell tumors, and stromal cell tumors, based on the kind of cells from which the tumor originates. The majority of ovarian cancers are thought to arise from the ovarian surface epithelium. The ovarian surface epithelium is a highly dynamic tissue which undergoes morphogenic changes. It has significant proliferative properties, as it must proliferate rapidly to cover the ovulatory site after ovulation of the ova. In addition, morphological and histochemical studies suggest that the ovarian surface epithelium has secretory, endocytotic and transport functions which are hormonally controlled (Blaustein and Lee (1979) *Oncol.* 8:34–43; Nicosia and Johnson (1983) *Int. J. Gynecol. Pathol.* 3:249–260; Papadaki and Beilby (1971) *J. Cell Sci.* 8:445–464; Anderson et al. (1976) *J. Morphol.* 150:135–164). Epithelial ovarian cancer has a distinctive pattern of spread: cancer cells may migrate through the peritoneum to produce multiple metastatic nodules in the visceral and parietal peritoneum and the hemidiaphragms. In addition cancer cells metastasize through the lymphatic and blood vessels to areas such as the liver, lung and brain.

Since ovarian cancers are generally not readily detectable by diagnostic techniques until the disease has progressed to a late stage of development (Siemens and Auersperg (1988) *J. Cellular Physiol.* 134:347–356), it is one of the most lethal of the gynecological malignancies. Although a number of potential tumor markers including the cancer antigen 125 (Ca-125) have been evaluated, nonspecificity of the antigens diminish their value as markers for primary ovarian cancer (Kudlacek et al. (1989) *Gyn. Onc.* 35:323–329; Rustin et al. (1989) *J. Clin. Onc.* 7:1667–1671; Sevelda et al. (1989) *Am. J. Obstet. Gynecol.* 161:1213–1216; Omar et al. (1989) *Tumor Biol.* 10:316–323). Thus, there is a vital need for tumor markers which can be used in the specific, early detection of ovarian cancer, the monitoring of cancer therapies, the immunodetection of ovarian tumors, and the development of probes for potential use in immunotherapy (Cantarow et al. (1981) *Int. J. Radiation Oncol. Biol. Phys.* 7:1095–1098).

Lung cancer is the leading cause of cancer death among both men and women. There will be an estimated 157,400 deaths from lung cancer in 2001, accounting for 28% of all cancer deaths. The one-year survival rate for lung cancer has increased from 34% in 1975 to about 41% in 1996. This increase is largely a result of better methods of surgery and some progress in chemotherapy and radiation therapy. The five-year survival rate for all stages of lung cancer combined is 14%. For those whose cancer is found and treated by surgery early, before it has spread to lymph nodes or the other organs, the average five-year survival rate is about 49%. However, only 15% of lung cancers are found at this early, localized stage. One type of lung cancer is small cell lung cancer (SCLC). The second type is non-small cell lung cancer NSCLC. In addition to the two main types of lung cancer, other tumors can occur in the lungs. Carcinoid tumors of the lung account for less than 5% of all lung tumors.

Lung cancer is the most common form of cancer in the world. Estimates for the year 1985 indicate that there were about 900,000 cases of lung cancer worldwide. (Parkin, et al., "Estimates of the worldwide incidence of eighteen major cancers in 1985," Int J Cancer 1993; 54:594–606). For the United States alone, 1993 projections placed the number of new lung cancer cases at 170,000, with a mortality of about 88%. (Boring, et al., "Cancer statistics," CA Cancer J Clin 1993; 43:7–26). Although the occurrence of breast cancer is slightly more common in the United States, lung cancer is second behind prostate cancer for males and third behind breast and colorectal cancers for women. Yet, lung cancer is the most common cause of cancer deaths.

The World Health Organization classifies lung cancer into four major histological types: (1) squamous cell carcinoma (SCC), (2) adenocarcinoma, (3) large cell carcinoma, and (4) small cell lung carcinoma (SCLC). (The World Health Organization, "The World Health Organization histological typing of lung tumours," Am J Clin Pathol 1982; 77:123–136). However, there is a great deal of tumor heterogeneity even within the various subtypes, and it is not uncommon for lung cancer to have features of more than one morphologic subtype. The term non-small cell lung carcinoma (NSCLC) includes squamous, adenocarcinoma and large cell carcinomas.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Based on the prevalence of these disorders and the lack of effective cures and early diagnostics, there currently exists a great need for methods and compositions which can serve as markers before the onset of symptoms and which can serve as a means for identifying therapeutics to treat and or cure these disorders.

The present invention provides methods and compositions for the diagnosis and treatment of tumorigenic and/or angiogenic disorders (e.g., lung tumors, colon tumors, breast tumors, ovarian tumors, hemangioma, and metastatic and angiogenic tumors). The present invention is based, at least in part, on the discovery that the fucosidase 32616 is differentially expressed in tumor and/or angiogenic tissue samples as compared to its expression in normal tissue samples. Specifically, 32616 was found to be up-regulated in proliferating endothelial cells as compared to arrested endothelial cells; in early stages of endothelial tube formation; and in various tumors and angiogenic tissues including hemangiomas as compared to normal tissues (see FIGS. 2 and 3). The present invention is also based, at least in part, on the discovery that the 32616 gene is significantly upregulated in breast, lung, colon, ovary and angiogenic tumors, as compared to normal tissue from these organs (see FIG. 4).

In one aspect, the invention provides methods for identifying a compound capable of treating a tumorigenic and/or angiogenic disease, e.g., lung tumors, colon tumors, breast tumors, ovarian tumors, hemangioma, and metastatic and angiogenic tumors. The method includes assaying the ability of the compound to modulate 32616 nucleic acid expression or 32616 polypeptide activity. In one embodiment, the ability of the compound to modulate 32616 nucleic acid expression or 32616 polypeptide activity is determined by detecting modulation of tumorigenesis or angiogenesis in a cell (e.g., an epithelial, endothelial, or stromal cell derived from lung, breast, ovary, or colon tissues or from hemangioma, and metastatic/angiogenic tumor tissues). In another embodiment, the ability of the compound to modulate 32616 nucleic acid expression or 32616 polypeptide activity is determined by detecting modulation of the breakdown of a metabolic intermediate, e.g., a polypeptide, a nucleic acid, an oligosaccharide, a glycopeptide, a glycoprotein, a glycolipid or a lipid in a cell.

In another aspect, the invention provides methods for identifying a compound capable of modulating tumorigenesis or angiogenesis. The method includes contacting a cell expressing a 32616 nucleic acid or polypeptide (e.g., an epithelial, endothelial, or stromal cell) with a test compound and assaying the ability of the test compound to modulate the expression of a 32616 nucleic acid or the activity of a 32616 polypeptide.

In a further aspect, the invention features a method for modulating tumorigenesis or angiogenesis. The method includes contacting a cell with a 32616 modulator, for example, an anti-32616 antibody, a 32616 polypeptide comprising the amino acid sequence of SEQ ID NO:2, or a fragment thereof, a 32616 polypeptide comprising an amino acid sequence which is at least 90 percent identical to the amino acid sequence of SEQ ID NO:2, an isolated naturally occurring allelic variant of a polypeptide consisting of the amino acid sequence of SEQ ID NO:2, a small molecule, an antisense 32616 nucleic acid molecule, a nucleic acid molecule of SEQ ID NO:1 or 3, or a fragment thereof, or a ribozyme.

In yet another aspect, the invention features a method for treating a subject having a tumorigenic and/or angiogenic disorder e.g., a tumorigenic and/or angiogenic disorder characterized by aberrant 32616 polypeptide activity or aberrant 32616 nucleic acid expression, such as a lung tumor, a colon tumor, a breast tumor, an ovarian tumor, a hemangioma, and a metastatic or angiogenic tumor. The method includes administering to the subject a therapeutically effective amount of a 32616 modulator (e.g., using a pharmaceutically acceptable formulation or a gene therapy vector). In one embodiment, the 32616 modulator may be a small molecule, an anti-32616 antibody, a 32616 polypeptide comprising the amino acid sequence of SEQ ID NO:2, or a fragment thereof, a 32616 polypeptide comprising an amino acid sequence which is at least 90 percent identical to the amino acid sequence of SEQ ID NO:2, an isolated naturally occurring allelic variant of a polypeptide consisting of the amino acid sequence of SEQ ID NO:2, an antisense 32616 nucleic acid molecule, a nucleic acid molecule of SEQ ID NO:1 or 3, or a fragment thereof, or a ribozyme.

In another aspect, the invention provides a method for modulating, e.g., increasing or decreasing, tumorigenesis and angiogenesis in a subject suffering from a tumorigenic and/or an angiogenic disorder by administering to the subject a therapeutically effective amount of a 32616 modulator. Other features and advantages of the invention will be apparent from the following detailed description and claims.

FIGS. 1A–B depict the cDNA sequence and predicted amino acid sequence of human 32616. The nucleotide sequence corresponds to nucleic acids 1 to 1710 of SEQ ID NO:1. The amino acid sequence corresponds to amino acids 1 to 390 of SEQ ID NO:2. The coding region without the 5' or 3' untranslated region of the human 32616 gene is set forth in SEQ ID NO:3.

The present invention provides methods and compositions for the diagnosis and treatment of tumorigenic and/or angiogenic disorders (e.g., lung tumors, colon tumors, breast tumors, ovarian tumors, hemangioma, and metastatic and angiogenic tumors).

Fucosidases are ubiquitous lysosomal glycosidases involved in the degradation of a diverse group of naturally occurring fucoglycoconjugates. Mammalian fucosidases are sialoglycoproteins and the carbohydrate content in these proteins, particularly sialic acid, contributes to the generation of multiple isoforms of a fucoside molecule. α-L-fucosidase exhibits substrate specificity primarily to galactose and N-acetylglucosamine. Numerous linkages, such as, α-1-2, α 1-3, α 1-4, α 1-6, present in galactose and N-acetylglucosamine molecules can be hydrolyzed by fucosidases. For example, α-L-fucosidase is highly effective in hydrolyzing small molecular weight water-soluble substrates with fucose in α 1-2 linkage to galactose. Fucosidases are very important in mammalian metabolism as evidenced by diseases in humans who lack a functional form of this enzyme.

Figure 2A:
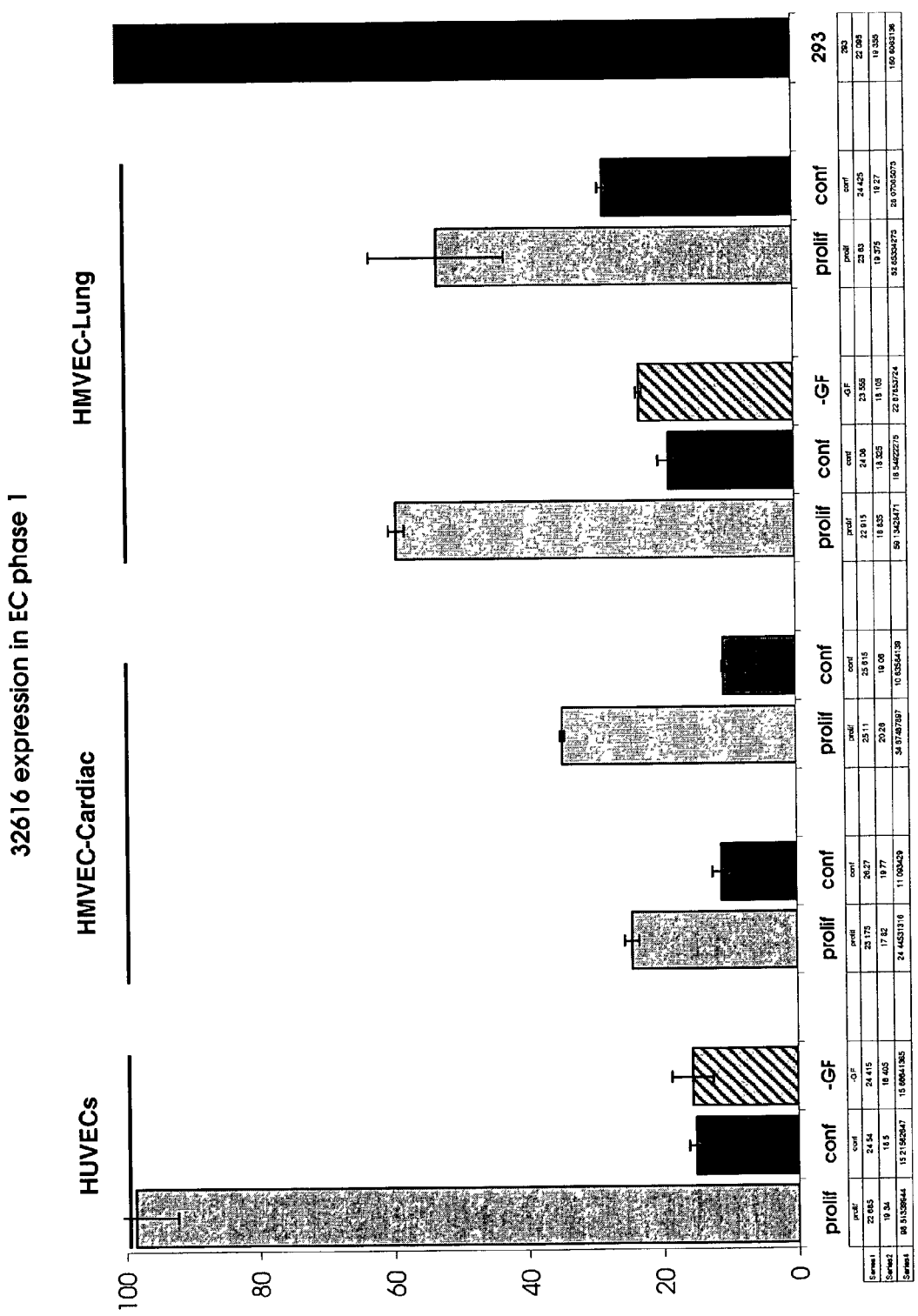
FIG. 2A is a graph showing upregulation of 32616 expression in proliferating endothelial cells, as determined by Taqman™ analysis.

The present invention is based, at least in part, on the discovery that the fucosidase 32616 is differentially expressed in tumor and/or angiogenic tissue samples as compared to its expression in normal tissue samples. Specifically, 32616 was found to be up-regulated in proliferating endothelial cells as compared to arrested endothelial cells, in early stages of endothelial tube formation; and in various tumors and angiogenic tissues including hemangiomas as compared to normal tissues (see FIGS. 2 and 3). The present invention is also based, at least in part, on the discovery that the 32616 gene is significantly upregulated in breast, lung, colon, ovary and angiogenic tumors, as compared to normal tissue from these organs (see FIG. 4).

Accordingly, the present invention provides methods and compositions for treating, diagnosing or prognosing tumorigenic/and or angiogenic disorders.

As used herein, a "tumorigenic disease or disorder" includes a disease or disorder characterized by aberrantly regulated cell growth, proliferation, differentiation, adhesion, or migration, resulting in the production of or tendency to produce tumors. As used herein, a "tumor" includes a normal benign or malignant mass of tissue. Examples of tumorigenic diseases include cancer, e.g., carcinoma, sarcoma, lymphoma or leukemia, examples of which include, but are not limited to, ovarian, lung, breast, endometrial, uterine, hepatic, gastrointestinal, prostate, colorectal, and brain cancer.

As used herein, the term angiogenic disease or disorder" includes a disease or disorder characterized by aberrantly regulated angiogenesis. As used herein, the term "angiogenesis" refers to the process by which new blood vessels, e.g., blood capillaries, vessels, and veins are formed. Key components of the angiogenic process are the degradation of the basement membrane, the migration and proliferation of capillary endothelial cell (EC) and the formation of three-dimensional capillary tubes. New blood vessels can develop from the walls of existing small vessels by the outgrowth of endothelial cells. Angiogenesis is also involved in tumor growth as it provides tumors with the blood supply necessary for tumor cell survival and proliferation (growth). Examples of angiogenic diseases include solid tumor growth and metastasis, psoriasis, endometriosis, Grave's disease, ischemic disease (e.g., atherosclerosis), and chronic inflammatory diseases (e.g., rheumatoid arthritis), and some types of eye disorders, (reviewed by Auerbach, et al., *J. Microvasc. Res.* 29:401–411 (1985); Folkman, Advances in Cancer Research, eds. Klein and Weinhouse, pp. 175–203 (Academic Press, New York, 1985); Patz, *Am. J. Opthalmol.* 94:715–743 (1982); and Folkman, et al., *Science* 221:719–725 (1983)). For example, there are a number of eye diseases, many of which lead to blindness, in which ocular neovascularization occurs in response to the diseased state. These ocular disorders include diabetic retinopathy, macular degeneration, neovascular glaucoma, inflammatory diseases and ocular tumors (e.g., retinoblastoma). There are a number of other eye diseases which are also associated with neovascularization, including retrolental fibroplasia, uveitis, eye diseases associated with choroidal neovascularization and eye diseases which are associated with iris neovascularization.

As used herein the term "angiogenic activity" refers to any activity, e.g., cellular activity, involved in or affecting angiogenesis.

As used herein the term "tumorigenic activity" refers to any activity, e.g., cellular activity, involved in or affecting the development of tumors.

As used herein the term, "hemangioma" includes different types of hemangioma or hemangioma-related disorders, such as, hemangioblast, hemangioblastoma, hemangioendothelioblastoma, hemangioendothelioma, hemangioendothelioma, epithelioid hemangioma, capillary hemangioma, hemangioma, cavernous hemangioma, hemangioma of bone, hemangioma of vertebrae, hemangiopericytoma, hemangiosarcoma.

"Differential expression", as used herein, includes both quantitative as well as qualitative differences in the temporal and/or tissue expression pattern of a gene. Thus, a differentially expressed gene may have its expression activated or inactivated in normal versus tumorigenic and/or angiogenic conditions (for example, in an experimental tumorigenic and/or angiogenic disease system). The degree to which expression differs in normal versus tumorigenic and/or angiogenic disease or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic tumorigenic and/or angiogenic disease evaluation, or may be used in methods for identifying compounds useful for the treatment of tumorigenic and/or angiogenic disease. In addition, a differentially expressed gene involved in a tumorigenic and/or angiogenic disease may represent a target gene such that modulation of the level of target gene expression or of target gene product activity may act to ameliorate a tumorigenic and/or angiogenic disease condition. Compounds that modulate target gene expression or activity of the target gene product can be used in the treatment of tumorigenic and/or angiogenic disease.

As used herein, the term "fucosidase" includes a molecule which is involved in the hydrolytic cleavage of a bond within a biological molecule (e.g., a peptide, a lipid, a nucleic acid, oligosaccharides, glycopeptides, glycoproteins, or glycolipids). Fucosidase molecules are involved in the anabolism and catabolism of metabolically important biomolecules, including the metabolism of biochemical molecules necessary for energy production or storage, and for intra- or inter-cellular signaling, as well as the detoxification of potentially harmful compounds (e.g., toxins, carcinogens).

As used interchangeably herein, an "32616 activity", "biological activity of 32616" or "32616-mediated activity", includes an activity exerted by a 32616 protein, polypeptide or nucleic acid molecule on a 32616 responsive cell or tissue, or on a 32616 protein substrate, as determined in vivo, or in vitro, according to standard techniques. In one embodiment, a 32616 activity is a direct activity, such as an association with a 32616 target molecule. As used herein, a "target molecule" or "binding partner" is a molecule with which a 32616 protein binds or interacts in nature, such that 32616 mediated function is achieved. A 32616 target molecule can be a non-32616 molecule or a 32616 protein or polypeptide. In an exemplary embodiment, a 32616 target molecule is a 32616 substrate (e.g., a peptide, a lipid, a nucleic acid, a vitamin, an oligosaccharide, a glycopeptide, a glycoprotein, or a glycolipid). Alternatively, a 32616 activity is an indirect activity, such as a cellular signaling activity mediated by interaction of the 32616 protein with a 32616 ligand or substrate. The biological activities of 32616 are described herein. For example, 32616 molecules may have one or more of the following activities: (1) they modulate the cleavage, e.g., hydrolytic cleavage, of a chemical bond within a biochemical molecule; (2) they cleave a biochemical molecule that is associated with the regulation of one or more tumor and/or angiogenic processes, such as a peptide, a nucleic acid, a lipid, a vitamin, an oligosaccharide, a glycopeptide, a glycoprotein, or a glycolipid, (3) they modulate the anabolism and catabolism of metabolically important biomolecules, including the metabolism of biochemical molecules necessary for energy production or storage, and for intra- or inter-cellular signaling, as well as the detoxification of potentially harmful compound.

I. Screening Assays:

The invention provides a method (also referred to herein as a "screening assay") for identifying modulators, i.e., candidate or test compounds or agents (e.g., peptides, peptidomimetics, small molecules or other drugs) which bind to 32616 proteins, have a stimulatory or inhibitory effect on, for example, 32616 expression or 32616 activity, or have a stimulatory or inhibitory effect on, for example, the expression or activity of a 32616 substrate.

Compounds identified via assays such as those described herein may be useful, for example, for ameliorating a 32616 associated disorder, such as, a tumorigenic and/or angiogenic disorder, e.g., cancer, and angiogenic disease. In instances whereby a tumorigenic and/or angiogenic disorder results from an overall lower level of 32616 gene expression and/or 32616 protein in a cell or tissue, compounds which accentuate or amplify the expression and/or activity of the 32616 protein may ameliorate symptoms. In other instances, mutations within the 32616 gene may cause aberrant types or excessive amounts of 32616 proteins to be made which have a deleterious effect that leads to a tumorigenic and/or angiogenic disease. Similarly, physiological conditions may cause an increase in 32616 gene expression leading to a tumorigenic and/or angiogenic disease. In such cases, compounds that inhibit or decrease the expression and/or activity of 32616 may ameliorate symptoms. Assays for testing the effectiveness of compounds identified by techniques are discussed herein.

In one embodiment, the invention provides assays for screening candidate or test compounds which are substrates of a 32616 protein or polypeptide or biologically active portion thereof (e.g., peptides, lipids, or nucleic acids). In another embodiment, the invention provides assays for screening candidate or test compounds which bind to or modulate the activity of a 32616 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner USP '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses a 32616 protein or biologically active portion thereof is contacted with a test compound and the ability of the test compound to modulate 32616 activity is determined. Determining the ability of the test compound to modulate 32616 activity can be accomplished by monitoring, for example, cell progression through the cell cycle, or the production of one or more specific metabolites in a cell which expresses 32616. The cell, for example, can be of mammalian origin, e.g., an epithelial or an endothelial cell. The ability of the test compound to modulate 32616 binding to a substrate (e.g., a peptide, lipid or nucleic acid) or to bind to 32616 can also be determined. Determining the ability of the test compound to modulate 32616 binding to a substrate can be accomplished, for example, by coupling the 32616 substrate with a radioisotope or enzymatic label such that binding of the 32616 substrate to 32616 can be determined by detecting the labeled 32616 substrate in a complex.

Cellular proliferation assays associated with tumorigenesis and/or angiogenesis that may be used to identify compounds that modulate 32616 activity include assays such as the acid phosphatase assay for cell number as described in Connolly et al. (1986) Anal. Biochem. 152, 136–140 and the MTT assay as described in Loveland, B. E. et al., (1992) Biochem. Int., 27:501–510, which utilizes calorimetric assays to quantitate viable cells, e.g., the cellular reduction of the tetrazolium salt, MTT, to formazan by mitochondrial succinate dehydrogenase. Other assays for cellular proliferation include clonogenic assays, assays for $^3$H-thymidine uptake, assays measuring the incorporation of radioactively labeled nucleotides into DNA, or other assays which are known in the art for measuring cellular proliferation. Moreover, inhibition of cellular growth in vivo, e.g., in a patient with cancer, can be detected by any standard method for detecting tumors such as by x-ray or imaging analysis of a tumor size, or by observing a reduction in mutant p53 protein production or in the production of any known cell-specific or tumor marker within a biopsy or tissue sample. Determining the ability of a test compound to modulate 32616 activity can be accomplished by monitoring, for example, cell progression through the cell cycle. For example, the cell can be a tumor cell, e.g., a colon tumor cell, a lung tumor cell, or an ovary tumor cell, a hemangioma, a metastatic or an angiogenic tumor.

In one aspect, an assay is a cell-based assay in which a cell which expresses a 32616 protein or biologically active portion thereof is contacted with a test compound and the ability of the test compound to modulate 32616 activity is determined. In a preferred embodiment, the biologically active portion of the 32616 protein includes a domain or motif that can modulate amino acid transport or degradation, cellular metabolism, or cellular growth or proliferation. Determining the ability of the test compound to modulate 32616 activity can be accomplished by monitoring, for example, the production of one or more specific metabolites (e.g., [$^3$H] mannose labelled-glycopeotides or a $^{14}$[C] fucose) in a cell which expresses 32616 (see, e.g., Nguyen M. et al. (1992) *J. Biol Chem.* 267: 26157–28165; Hitoshi S. et al. (1996) *J. Neurochem.* 66: 1633–1640) or by monitoring cell metabolism, cellular growth, cellular proliferation, or cellular differentiation. The cell, for example, can be of mammalian origin, e.g., a tumor cell such as a lung, ovary, colon tumor cell, a hemangioma, a metastatic or an angiogenic tumor.

Alternatively, 32616 could be coupled with a radioisotope or enzymatic label to monitor the ability of a test compound to modulate 32616 binding to a 32616 substrate in a complex. Determining the ability of the test compound to bind 32616 can be accomplished, for example, by coupling the compound with a radioisotope or enzymatic label such that binding of the compound to 32616 can be determined by detecting the labeled compound in a complex. For example, compounds (e.g., 32616 substrates) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a 32616 substrate) to interact with 32616 without the labeling of any of the interactants. For example, a microphysiometer can be used to detect the interaction of a compound with 32616 without the labeling of either the compound or the 32616. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32616.

In another embodiment, an assay is a cell-based assay comprising contacting a cell expressing a 32616 target molecule (e.g., a 32616 substrate) with a test compound and determining the ability of the test compound to modulate (e.g., stimulate or inhibit) the activity of the 32616 target molecule. Determining the ability of the test compound to modulate the activity of a 32616 target molecule can be accomplished, for example, by determining the ability of the 32616 protein to bind to or interact with the 32616 target molecule.

Determining the ability of the 32616 protein, or a biologically active fragment thereof, to bind to or interact with a 32616 target molecule can be accomplished by one of the methods described above for determining direct binding. In a preferred embodiment, determining the ability of the 32616 protein to bind to or interact with a 32616 target molecule can be accomplished by determining the activity of the target molecule. For example, the activity of the target molecule can be determined by detecting induction of a cellular response (i.e., cell proliferation, migration, survival activity, cell adhesion, vasculature or generation of new blood supply), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a 32616 protein or biologically active portion thereof is contacted with a test compound and the ability of the test compound to bind to the 32616 protein or biologically active portion thereof is determined. Preferred biologically active portions of the 32616 proteins to be used in assays of the present invention include fragments which participate in interactions with non-32616 molecules, e.g., fragments with high surface probability scores. Binding of the test compound to the 32616 protein can be determined either directly or indirectly as described above. In a preferred embodiment, the assay includes contacting the 32616 protein or biologically active portion thereof with a known compound which binds 32616 to form an assay mixture, contacting the assay mixture with a test compound, and determining the ability of the test compound to interact with a 32616 protein, wherein determining the ability of the test compound to interact with a 32616 protein comprises determining the ability of the test compound to preferentially bind to 32616 or biologically active portion thereof as compared to the known compound.

In another embodiment, the assay is a cell-free assay in which a 32616 protein or biologically active portion thereof is contacted with a test compound and the ability of the test compound to modulate (e.g., stimulate or inhibit) the activity of the 32616 protein or biologically active portion thereof is determined. Determining the ability of the test compound to modulate the activity of a 32616 protein can be accomplished, for example, by determining the ability of the 32616 protein to bind to a 32616 target molecule by one of the methods described above for determining direct binding. Determining the ability of the 32616 protein to bind to a 32616 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a 32616 protein can be accomplished by determining the ability of the 32616 protein to further modulate the activity of a downstream effector of a 32616 target molecule. For example, the activity of the effector molecule on an appropriate target can be determined or the binding of the effector to an appropriate target can be determined as previously described.

In yet another embodiment, the cell-free assay involves contacting a 32616 protein or biologically active portion thereof with a known compound (e.g., a 32616 substrate) which binds the 32616 protein to form an assay mixture, contacting the assay mixture with a test compound, and determining the ability of the test compound to interact with the 32616 protein, wherein determining the ability of the test compound to interact with the 32616 protein comprises determining the ability of the 32616 protein to preferentially bind to or modulate the activity of a 32616 target protein, e.g., catalyze the cleavage, e.g., the hydrolytic cleavage, of a chemical bond within the target protein.

In more than one embodiment of the above assay methods of the present invention, it may be desirable to immobilize either 32616 or its target molecule to facilitate separation of complexed from uncomplexed forms of one or both of the proteins, as well as to accommodate automation of the assay. Binding of a test compound to a 32616 protein, or interaction of a 32616 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/32616 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 32616 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 32616 binding or activity determined using standard techniques.

Other techniques for immobilizing proteins on matrices can also be used in the screening assays of the invention. For example, either a 32616 protein or a 32616 target molecule can be immobilized utilizing conjugation of biotin and streptavidin. Biotinylated 32616 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 32616 protein or target molecules but which do not interfere with binding of the 32616 protein to its target molecule can be derivatized to the wells of the plate, and unbound target or 32616 protein trapped in the wells by antibody conjugation. Methods for detecting such complexes, in addition to those described above for the GST-immobilized complexes, include immunodetection of complexes using antibodies reactive with the 32616 protein or target molecule, as well as enzyme-linked assays which rely on detecting an enzymatic activity associated with the 32616 protein or target molecule.

In another embodiment, modulators of 32616 expression are identified in a method wherein a cell is contacted with a candidate compound and the expression of 32616 mRNA or protein in the cell is determined. The level of expression of 32616 mRNA or protein in the presence of the candidate compound is compared to the level of expression of 32616 mRNA or protein in the absence of the candidate compound. The candidate compound can then be identified as a modulator of 32616 expression based on this comparison. For example, when expression of 32616 mRNA or protein is greater (statistically significantly greater) in the presence of the candidate compound than in its absence, the candidate compound is identified as a stimulator of 32616 mRNA or protein expression. Alternatively, when expression of 32616 mRNA or protein is less (statistically significantly less) in the presence of the candidate compound than in its absence, the candidate compound is identified as an inhibitor of 32616 mRNA or protein expression. The level of 32616 mRNA or protein expression in the cells can be determined by methods described herein for detecting 32616 mRNA or protein.

In yet another aspect of the invention, the 32616 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with 32616 ("32616 binding proteins" or "32616-bp") and are involved in 32616 activity. Such 32616 binding proteins are also likely to be involved in the propagation of signals by the 32616 proteins or 32616 targets as, for example, downstream elements of a 32616-mediated signaling pathway. Alternatively, such 32616 binding proteins are likely to be 32616 inhibitors.

The two-hybrid system is based on the modular nature of most transcription factors, which consist of separable DNA-binding and activation domains. Briefly, the assay utilizes two different DNA constructs. In one construct, the gene that codes for a 32616 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 32616-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32616 protein.

In another aspect, the invention pertains to a combination of two or more of the assays described herein. For example, a modulating agent can be identified using a cell-based or a cell free assay, and the ability of the agent to modulate the activity of a 32616 protein can be confirmed in vivo, e.g., in an animal such as an animal model for tumorigenesis and/or angiogenesis.

This invention further pertains to novel agents identified by the above-described screening assays. Accordingly, it is within the scope of this invention to further use an agent identified as described herein in an appropriate animal model. For example, an agent identified as described herein (e.g., a 32616 modulating agent, an antisense 32616 nucleic acid molecule, a 32616-specific antibody, or a 32616 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate symptoms of, for example, a tumorigenic and/or angiogenic disorder. Cell-based and animal model-based assays for the identification of compounds exhibiting an ability to ameliorate the symptoms of a tumorigenic and/or angiogenic disorder are described herein.

In one aspect, cell-based systems, as described herein, may be used to identify compounds which may act to ameliorate symptoms of a tumorigenic and/or angiogenic disorder. For example, such cell systems may be exposed to a test compound (e.g., suspected of exhibiting an ability to ameliorate symptoms of a tumorigenic and/or angiogenic disorder), at a sufficient concentration and for a time sufficient to elicit amelioration of symptoms of a tumorigenic and/or angiogenic disorder in the exposed cells. After exposure, the cells are examined to determine whether one or more of the cellular phenotypes associated with a tumorigenic and/or angiogenic disorder has been altered to resemble a normal or wild type, non-tumorigenic and/or non-angiogenic disorder phenotype. Cellular phenotypes that are associated with tomorigenic/angiogenicinclude aberrant proliferation and survival, migration, anchorage independent growth, loss of contact inhibition, loss of cell adhesion, vasculature or generation of new blood supply.

In addition, animal-based models of tumorigenic and/or angiogenic disorders, such as those described herein, may be used to identify compounds capable of ameliorating symptoms of a tumorigenic and/or angiogenic disorder.

Such animal models may also be used to test substrates for the identification of drugs, pharmaceuticals, therapies, and interventions which may be effective in treating a tumorigenic and/or angiogenic disorder. For example, animal models may be exposed to a test compound at a sufficient concentration and for a time sufficient to ameliorate symptoms of a tumorigenic and/or angiogenic disorder in the exposed animals. The response of the animals to the exposure may be monitored by assessing amelioration of symptoms of a tumorigenic and/or angiogenic disorder, for example, reduction in tumor size, invasive and/or metastatic potential, as well as tumor burden, before and after treatment.

With regard to intervention, any treatments which reverse any aspect of a tumorigenic and/or angiogenic disorder should be considered as candidates for human disease therapeutic intervention. Dosages of test agents may be determined by deriving dose-response curves.

Additionally, gene expression patterns may be utilized to assess the ability of a compound to ameliorate symptoms of a tumorigenic and/or angiogenic disorder. For example, the expression pattern of one or more genes may form part of a "gene expression profile" or "transcriptional profile" which may be then in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis and metastasis. Gene expression profiles may be generated, for example, by utilizing a differential display procedure, Northern analysis and/or RT-PCR. In one embodiment, 32616 gene sequences may be used as probes and/or PCR primers for the generation and corroboration of such gene expression profiles.

Gene expression profiles may be characterized for known states, for example, a tumorigenic and/or angiogenic state or normal state, within the cell- and/or animal-based model systems. Subsequently, these known gene expression profiles may be compared to ascertain the effect of a test compound on modifying such gene expression profiles.

For example, administration of a test compound may cause the gene expression profile of a tumorigenic and/or angiogenic disorder model system to more closely resemble the control system. Administration of a test compound may, alternatively, cause the gene expression profile of a control system to begin to mimic a tumorigenic and/or angiogenic disorder state. Such a test compound may, for example, be used in further characterizing the test compound of interest, or may be used in the generation of additional animal models.

Cells that contain and express 32616 gene sequences which encode a 32616 protein, and further, exhibit cellular phenotypes associated with a tumorigenic and/or angiogenic disorder, may be used to identify compounds that exhibit cellular growth modulatory activity. Such cells include tumor cell lines, such as those exemplified herein, as well as generic mammalian cell lines such as COS cells. Further, such cells may include recombinant cell lines derived from a transgenic (e.g., immortalized cell lines derived from 32616 transgenic mice in which 32616 expression is regulated by the rat insulin promoter regulated simian virus 40 T antigen) or a knockout animal (e.g., p53−/− tumor susceptible animal). For example, animal models of tumorigenesis and/or angiogenesis, such as those discussed above, may be used to generate cell lines that can be used as cell culture models for this disorder. While primary cultures derived from transgenic or knockout animals may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in tumorigenic and/or angiogenic disorder may be transfected with sequences capable of increasing or decreasing the amount of 32616 gene expression within the cell. For example, 32616 gene sequences may be introduced into, and overexpressed in, the genome of the cell of interest, or, if endogenous 32616 gene sequences are present, they may be either overexpressed or, alternatively, disrupted in order to underexpress or inactivate 32616 gene expression.

In order to overexpress a 32616 gene, the coding portion of the 32616 gene may be ligated to a regulatory sequence which is capable of driving gene expression in the cell type of interest. Such regulatory regions will be well known to those of skill in the art, and may be utilized in the absence of undue experimentation. Recombinant methods for expressing target genes are described above.

For underexpression of an endogenous 32616 gene sequence, such a sequence may be isolated and engineered such that when reintroduced into the genome of the cell type of interest, the endogenous 32616 alleles will be inactivated. Preferably, the engineered 32616 sequence is introduced via gene targeting such that the endogenous 32616 sequence is disrupted upon integration of the engineered 32616 sequence into the cell's genome. Transfection of host cells with 32616 genes is discussed, above.

Cells treated with test compounds or transfected with 32616 genes can be examined for phenotypes associated with a tumorigenic and/or angiogenic disorder, e.g., dysregulated proliferation and migration, anchorage independent growth, loss of contact inhibition, loss of cell adhesion, vasculature, and generation of new blood supply.

Transfection of a 32616 nucleic acid may be accomplished by using standard techniques (described herein and in, for example, Ausubel (1989) supra). Transfected cells should be evaluated for the presence of the recombinant 32616 gene sequences, for expression and accumulation of 32616 mRNA, and for the presence of recombinant 32616 protein production. In instances wherein a decrease in 32616 gene expression is desired, standard techniques may be used to demonstrate whether a decrease in endogenous 32616 gene expression and/or in 32616 protein production is achieved.

Cellular models for the study of tumorigenic and/or angiogenic disorder are known in the art, and include cell lines derived from clinical tumors, cells exposed to carcinogenic agents, and cell lines with genetic alterations in growth regulatory genes, for example, oncogenes (e.g., ras) and tumor suppressor genes (e.g., p53).

In another aspect, the invention pertains to a combination of two or more of the assays described herein. For example, a modulating agent can be identified using a cell-based or a cell-free assay, and the ability of the agent to modulate the activity of a 32616 protein can be confirmed in vivo, e.g., in an animal such as an animal model for a cellular proliferation disorder, e.g., cancer. Examples of animal models of cancer include transplantable models (e.g., xenografts). Xenografts for colon cancer can be performed with the following cell lines: HCT-116, HT-29, SW-480, SW-620, Colon 26, DLD1, Caco2, colo205, T84, and KM12. Xenografts for lung cancer can be performed with the following cell lines: NCI-H125, NCI-H460, A549, NCI-H69, and NCI-H345. Xenografts for ovarian cancer can be performed with the SKOV3 and HEY cell lines. Xenografts for breast cancer can be performed with, for example, MCF10AT cells, which can be grown as subcutaneous or orthotopic (cleared mammary fat pad) xenografts in mice. MCF10AT xenografts produce tumors that progress in a manner analogous to human breast cancer. Estrogen stimulation has also been shown to accelerate tumor progression in this model. MCF10AT xenografted tumors representing stages hyperplasia, carcinoma in situ, and invasive carcinoma will be isolated expression profiling. A metastatic subclone of the human breast cancer cell line MDA-MB-231 that metastasizes to brain, lung and bone can also be grown in vitro and in vivo at various sites (i.e. subcutaneously, orthotopically, in bone following direct bone injection, in bone following intracardiac injection). MCF-7 and T-47D are other mammary adenocarcinoma cell lines that can be grown as xenografts. All of these cells can be transplanted into immunocompromised mice such as SCID or nude mice, for example.

Orthotopic metastasis mouse models may also be utilized. For example, the HCT-116 human colon carcinoma cell line can be grown as a subcutaneous or orthotopic xenograft (intracaecal injection) in athymic nude mice. Rare liver and lung metastases can be isolated, expanded in vitro, and re-implanted in vivo. A limited number of iterations of this process can be employed to isolate highly metastatic variants of the parental cell line. Standard and subtracted cDNA libraries and probes can be generated from the parental and variant cell lines to identify genes associated with the acquisition of a metastatic phenotype. This model can be established using several alternative human colon carcinoma cell lines, including SW480 and KM12C.

Also useful in the methods of the invention are mis-match repair models (MMRs). Hereditary nonpolyposis colon cancer (HNPCC), which is caused by germline mutations in MSH2 & MLH1, genes involved in DNA mismatch repair, accounts for 5–15% of colon cancer cases. Mouse models have been generated carrying null mutations in the MLH1, MSH2 and MSH3 genes.

Other animal models for cancer (e.g., tumorigenic and/or angiogenic) include transgenic models (e.g., B66-Min/+ mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) Anticancer Res 20(2A):715; and cancer cell implantation or inoculation models as described in, for example, Fingert et al. (1987) Cancer Res 46(14):3824–9 and Teraoka et al. (1995) Jpn J Cancer Res 86(5):419–23. RIP-Tag model (Hanahan, D. (1985) Nature 315, 115–122). Furthermore, experimental model systems are available for the study of, for example, ovarian cancer (Hamilton, T C et al. Semin Oncol (1984) 11:285–298; Rahman, N A et al. Mol Cell Endocrinol (1998) 145:167–174; Beamer, W G et al. Toxicol Pathol (1998) 26:704–710), gastric cancer (Thompson, J et al. Int J Cancer (2000) 86:863–869; Fodde, R et al. Cytogenet Cell Genet (1999) 86:105–111), breast cancer (Li, M et al. Oncogene (2000) 19:1010–1019; Green, J E et al. Oncogene (2000) 19:1020–1027), melanoma (Satyamoorthy, K et al. Cancer Metast Rev (1999) 18:401–405), and prostate cancer (Shirai, T et al. Mutat Res (2000) 462: 219–226; Bostwick, D G et al. Prostate (2000) 43:286–294). Mouse models for colon cancer include the $APC^{min}$ mouse, a highly characterized genetic model of human colorectal carcinogeneis; the $APC^{1638}N$ mouse, which was generated by introducing a PGK-neomycin gene at codon 1638 of the APC gene and develops aberrant crypt foli after 6–8 weeks which ultimately progress to carcinomas by 4 months of age; and the $p53^{-/-}$ mouse which develops colon carcinomas that histopathologically resemble human disease.

Other animal based models for studying tumorigenesis in vivo are well known in the art (reviewed in Animal Models of Cancer Predisposition Syndromes, Hiai, H and Hino, O (eds.) 1999, Progress in Experimental Tumor Research, Vol. 35; Clarke A R Carcinogenesis (2000) 21:435–41) and include, for example, carcinogen-induced tumors (Rithidech, K et al. Mutat Res (1999) 428:33–39; Miller, M L et al. Environ Mol Mutagen (2000) 35:319–327), injection and/or transplantation of tumor cells into an animal, as well as animals bearing mutations in growth regulatory genes, for example, oncogenes (e.g., ras) (Arbeit, J M et al. Am J Pathol (1993) 142:1187–1197; Sinn, E et al. Cell (1987) 49:465–475; Thorgeirsson, S S et al. Toxicol Lett (2000) 112–113:553–555) and tumor suppressor genes (e.g., p53) (Vooijs, M et al. Oncogene (1999) 18:5293–5303; Clark A R Cancer Metast Rev (1995) 14:125–148; Kumar, T R et al. J Intern Med (1995) 238:233–238; Donehower, L A et al. (1992) Nature 356215–221). Furthermore, experimental model systems are available for the study of, for example, ovarian cancer (Hamilton, T C et al. Semin Oncol (1984) 11:285–298; Rahman, N A et al. Mol Cell Endocrinol (1998) 145:167–174; Beamer, W G et al. Toxicol Pathol (1998) 26:704–710), gastric cancer (Thompson, J et al. Int J Cancer (2000) 86:863–869; Fodde, R et al. Cytogenet Cell Genet (1999) 86:105–111), breast cancer (Li, M et al. Oncogene (2000) 19:1010–1019; Green, J E et al. Oncogene (2000) 19:1020–1027), melanoma (Satyamoorthy, K et al. Cancer Metast Rev (1999) 18:401–405), and prostate cancer (Shirai, T et al. Mutat Res (2000) 462:219–226; Bostwick, D G et al. Prostate (2000) 43:286–294).

Additionally, gene expression patterns may be utilized to assess the ability of a compound to ameliorate tumorigenic and/or angiogenic disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell proliferation, differentiation, transformation, tumorigenesis, metastasis, and carcinogen exposure. Gene expression profiles may be generated, for example, by utilizing a differential display procedure, Northern analysis and/or RT-PCR. In one embodiment, 32616 gene sequences may be used as probes and/or PCR primers for the generation and corroboration of such gene expression profiles.

Gene expression profiles may be characterized for known states, such as, tumorigenic and/or angiogenic disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a tumorigenic and/or angiogenic disease model system to more closely resemble the control system. Administration of a compound may, alternatively, cause the gene expression profile of a control system to begin to mimic a tumorigenic and/or angiogenic disease state. Such a compound may, for example, be used in further characterizing the compound of interest, or may be used in the generation of additional animal models.

Models for studying tumorigenesis and/or angiogenesis in vivo include carcinogen-induced tumors, injection and/or transplantation of tumor cells into an animal, as well as animals bearing mutations in growth regulatory genes.

II. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 32616 protein and/or nucleic acid expression as well as 32616 activity, in the context of a biological sample (e.g., blood, serum, cells, tissue) to thereby determine whether an individual is afflicted with a disease or disorder, or is at risk of developing a disorder, associated with aberrant or unwanted 32616 expression or activity, e.g., a tumorigenic and/or angiogenic disorder. The invention also provides for prognostic (or predictive) assays for determining whether an individual is at risk of developing a disorder associated with 32616 protein, nucleic acid expression or activity. For example, mutations in a 32616 gene can be assayed in a biological sample. Such assays can be used for prognostic or predictive purpose to thereby phophylactically treat an individual prior to the onset of a disorder characterized by or associated with 32616 protein, nucleic acid expression or activity.

Another aspect of the invention pertains to monitoring the influence of agents (e.g., drugs, compounds) on the expression or activity of 32616 in clinical trials.

These and other agents are described in further detail in the following sections.

A. Diagnostic Assays for Tumorigenic and/or angiogenic Disorders

An exemplary method for detecting the presence or absence of 32616 protein or nucleic acid in a biological sample involves obtaining a biological sample from a test subject and contacting the biological sample with a compound or an agent capable of detecting 32616 protein or nucleic acid (e.g., mRNA, or genomic DNA) that encodes 32616 protein such that the presence of 32616 protein or nucleic acid is detected in the biological sample. A preferred agent for detecting 32616 mRNA or genomic DNA is a labeled nucleic acid probe capable of hybridizing to 32616 mRNA or genomic DNA. The nucleic acid probe can be, for example, the 32616 nucleic acid set forth in SEQ ID NO:1 or 3, or a portion thereof, such as an oligonucleotide of at least 15, 30, 50, 100, 250 or 500 nucleotides in length and sufficient to specifically hybridize under stringent conditions to 32616 mRNA or genomic DNA. Other suitable probes for use in the diagnostic assays of the invention are described herein.

A preferred agent for detecting 32616 protein is an antibody capable of binding to 32616 protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect 32616 mRNA, protein, or genomic DNA in a biological sample in vitro as well as in vivo. For example, in vitro techniques for detection of 32616 mRNA include Northern hybridizations and in situ hybridizations. In vitro techniques for detection of 32616 protein include enzyme linked immunosorbent assays (ELISAs), Western blots, immunoprecipitations and immunofluorescence. In vitro techniques for detection of 32616 genomic DNA include Southern hybridizations. Furthermore, in vivo techniques for detection of 32616 protein include introducing into a subject a labeled anti-32616 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting 32616 protein, mRNA, or genomic DNA, such that the presence of 32616 protein, mRNA or genomic DNA is detected in the biological sample, and comparing the presence of 32616 protein, mRNA or genomic DNA in the control sample with the presence of 32616 protein, mRNA or genomic DNA in the test sample.

The invention also encompasses kits for detecting the presence of 32616 in a biological sample. For example, the kit can comprise a labeled compound or agent capable of detecting 32616 protein or mRNA in a biological sample; means for determining the amount of 32616 in the sample; and means for comparing the amount of 32616 in the sample with a standard. The compound or agent can be packaged in a suitable container. The kit can further comprise instructions for using the kit to detect 32616 protein or nucleic acid.

B. Prognostic Assays for Tumorigenic and/or Angiogenic Disorders

The diagnostic methods described herein can furthermore be utilized to identify subjects having or at risk of developing a disease or disorder associated with aberrant or unwanted 32616 expression or activity, e.g., a tumorigenic and/or angiogenic disorder. As used herein, the term "aberrant" includes a 32616 expression or activity which deviates from the wild type 32616 expression or activity. Aberrant expression or activity includes increased or decreased expression or activity, as well as expression or activity which does not follow the wild type developmental pattern of expression or the subcellular pattern of expression. For example, aberrant 32616 expression or activity is intended to include the cases in which a mutation in the 32616 gene causes the 32616 gene to be under-expressed or over-expressed and situations in which such mutations result in a non-functional 32616 protein or a protein which does not function in a wild-type fashion, e.g., a protein which does not interact with a 32616 substrate, or one which interacts with a non-32616 substrate.

As used herein, the term "unwanted" includes an unwanted phenomenon involved in a biological response such as cellular proliferation. For example, the term unwanted includes a 32616 expression or activity which is undesirable in a subject.

The assays described herein, such as the preceding diagnostic assays or the following assays, can be utilized to identify a subject having or at risk of developing a disorder associated with a misregulation in 32616 protein activity or nucleic acid expression, such as a cell proliferation, growth, differentiation, survival, or migration disorder. Alternatively, the prognostic assays can be utilized to identify a subject having or at risk for developing a disorder associated with a misregulation in 32616 protein activity or nucleic acid expression, such as a cell proliferation, growth, differentiation, survival, or migration disorder. Thus, the present invention provides a method for identifying a disease or disorder associated with aberrant or unwanted 32616 expression or activity in which a test sample is obtained from a subject and 32616 protein or nucleic acid (e.g., mRNA or genomic DNA) is detected, wherein the presence of 32616 protein or nucleic acid is diagnostic for a subject having or at risk of developing a disease or disorder associated with aberrant or unwanted 32616 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32616 expression or activity. For example, such methods can be used to determine whether a subject can be effectively treated with an agent for a cell proliferation, growth, differentiation, survival, or migration disorder. Thus, the present invention provides methods for determining whether a subject can be effectively treated with an agent for a disorder associated with aberrant or unwanted 32616 expression or activity in which a test sample is obtained and 32616 protein or nucleic acid expression or activity is detected (e.g., wherein the abundance of 32616 protein or nucleic acid expression or activity is diagnostic for a subject that can be administered the agent to treat a disorder associated with aberrant or unwanted 32616 expression or activity).

The methods of the invention can also be used to detect genetic alterations in a 32616 gene, thereby determining if a subject with the altered gene is at risk for a disorder characterized by misregulation in 32616 protein activity or nucleic acid expression, such as a cell proliferation, growth, differentiation, survival, or migration disorder. In preferred embodiments, the methods include detecting, in a sample of cells from the subject, the presence or absence of a genetic alteration characterized by at least one of an alteration affecting the integrity of a gene encoding a 32616 protein, or the mis-expression of the 32616 gene. For example, such genetic alterations can be detected by ascertaining the existence of at least one of 1) a deletion of one or more nucleotides from a 32616 gene; 2) an addition of one or more nucleotides to a 32616 gene; 3) a substitution of one or more nucleotides of a 32616 gene, 4) a chromosomal rearrangement of a 32616 gene; 5) an alteration in the level of a messenger RNA transcript of a 32616 gene, 6) aberrant modification of a 32616 gene, such as of the methylation pattern of the genomic DNA, 7) the presence of a non-wild type splicing pattern of a messenger RNA transcript of a 32616 gene, 8) a non-wild type level of a 32616 protein, 9) allelic loss of a 32616 gene, and 10) inappropriate post-translational modification of a 32616 protein. As described herein, there are a large number of assays known in the art which can be used for detecting alterations in a 32616 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a 32616 gene (see Abravaya et al. (1995) Nucleic Acids Res 0.23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a 32616 gene under conditions such that hybridization and amplification of the 32616 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874–1878), transcriptional amplification system (Kwoh, D. Y. et al., (1989) Proc. Natl. Acad. Sci. USA 86:1173–1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 32616 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32616 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 32616 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32616 gene and detect mutations by comparing the sequence of the sample 32616 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the 32616 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type 32616 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 32616 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 32616 sequence, e.g., a wild-type 32616 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 32616 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 32616 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32616 gene.

Furthermore, any cell type or tissue in which 32616 is expressed may be utilized in the prognostic assays described herein.

C. Monitoring of Effects During Clinical Trials

Monitoring the influence of agents (e.g., drugs) on the expression or activity of a 32616 protein (e.g., the modulation of cell proliferation, migration, adhesion, survival, vasculature, and generation of new blood supply) can be applied not only in basic drug screening, but also in clinical trials. For example, the effectiveness of an agent determined by a screening assay as described herein to increase 32616 gene expression, protein levels, or upregulate 32616 activity, can be monitored in clinical trials of subjects exhibiting decreased 32616 gene expression, protein levels, or down-regulated 32616 activity. Alternatively, the effectiveness of an agent determined by a screening assay to decrease 32616 gene expression, protein levels, or downregulate 32616 activity, can be monitored in clinical trials of subjects exhibiting increased 32616 gene expression, protein levels, or upregulated 32616 activity. In such clinical trials, the expression or activity of a 32616 gene, and preferably, other genes that have been implicated in, for example, a 32616-associated disorder can be used as a "read out" or markers of the phenotype of a particular cell.

For example, and not by way of limitation, genes, including 32616, that are modulated in cells by treatment with an agent (e.g., compound, drug or small molecule) which modulates 32616 activity (e.g., identified in a screening assay as described herein) can be identified. Thus, to study the effect of agents on 32616-associated disorders (e.g., disorders characterized by deregulated cell proliferation, migration, adhesion, survival, vasculature, and generation of new blood supply), for example, in a clinical trial, cells can be isolated and RNA prepared and analyzed for the levels of expression of 32616 and other genes implicated in the 32616-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of 32616 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a 32616 protein, mRNA, or genomic DNA in the preadministration sample; (iii) obtaining one or more post-administration samples from the subject; (iv) detecting the level of expression or activity of the 32616 protein, mRNA, or genomic DNA in the post-administration samples; (v) comparing the level of expression or activity of the 32616 protein, mRNA, or genomic DNA in the pre-administration sample with the 32616 protein, mRNA, or genomic DNA in the post administration sample or samples; and (vi) altering the administration of the agent to the subject accordingly. For example, increased administration of the agent may be desirable to increase the expression or activity of 32616 to higher levels than detected, i.e., to increase the effectiveness of the agent. Alternatively, decreased administration of the agent may be desirable to decrease expression or activity of 32616 to lower levels than detected, i.e. to decrease the effectiveness of the agent. According to such an embodiment, 32616 expression or activity may be used as an indicator of the effectiveness of an agent, even in the absence of an observable phenotypic response.

III. Methods of Treatment of Subjects Suffering from Tumorigenic and/or Angiogenic Disorders:

The present invention provides for both prophylactic and therapeutic methods of treating a subject at risk of (or susceptible to) a disorder or having a disorder associated with aberrant or unwanted 32616 expression or activity, e.g., a fucosidase-associated disorder such as a tumorigenic and/or angiogenic. The term "treatment", as used herein, is defined as the application or administration of a therapeutic agent to a patient, or application or administration of a therapeutic agent to an isolated tissue or cell line from a patient, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder, e.g., a tumorigenic and/or angiogenic disorder. A therapeutic agent includes, but is not limited to, small molecules, peptides, antibodies, ribozymes and antisense oligonucleotides With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the 32616 molecules of the present invention or 32616 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the invention provides a method for preventing in a subject, a disease or condition associated with an aberrant or unwanted 32616 expression or activity, by administering to the subject a 32616 or an agent which modulates 32616 expression or at least one 32616 activity. Subjects at risk for a disease which is caused or contributed to by aberrant or unwanted 32616 expression or activity can be identified by, for example, any or a combination of diagnostic or prognostic assays as described herein. Administration of a prophylactic agent can occur prior to the manifestation of symptoms characteristic of the 32616 aberrancy, such that a disease or disorder is prevented or, alternatively, delayed in its progression. Depending on the type of 32616 aberrancy, for example, a 32616, 32616 agonist or 32616 antagonist agent can be used for treating the subject. The appropriate agent can be determined based on screening assays described herein.

B. Therapeutic Methods

Another aspect of the invention pertains to methods for treating a subject suffering from a tumorigenic and/or angiogenic disorder. These methods involve administering to a subject an agent which modulates 32616 expression or activity (e.g., an agent identified by a screening assay described herein), or a combination of such agents. In another embodiment, the method involves administering to a subject a 32616 protein or nucleic acid molecule as therapy to compensate for reduced, aberrant, or unwanted 32616 expression or activity.

Stimulation of 32616 activity is desirable in situations in which 32616 is abnormally downregulated and/or in which increased 32616 activity is likely to have a beneficial effect, i.e., a decrease in cell proliferation or survival, thereby ameliorating a tumorigenic and/or angiogenic disorder that may be related with disease such as, AIDS or immunosupressive disorders. Likewise, inhibition of 32616 activity is desirable in situations in which 32616 is abnormally upregulated and/or in which decreased 32616 activity is likely to have a beneficial effect, e.g., a decrease in cell proliferation or survival, thereby ameliorating a tumorigenic and/or angiogenic disorder such as tumor.

The agents which modulate 32616 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 32616 activity (e.g., a fragment of a 32616 protein or an anti-32616 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 32616 activity can also be prepared in the form of suppositories (e.g., with conventional suppository bases such as cocoa butter and other glycerides) or retention enemas for rectal delivery.

In one embodiment, the agents that modulate 32616 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 32616 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 32616 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg cellular proliferative, preferably about 0.01 to 25 mg/kg cellular proliferative, more preferably about 0.1 to 20 mg/kg cellular proliferative, and even more preferably about 1 to 10 mg/kg, 2 to 9 mg/kg, 3 to 8 mg/kg, 4 to 7 mg/kg, or 5 to 6 mg/kg cellular proliferative. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg cellular proliferative, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, cellular proliferative, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

C. Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 32616 activity, as well as tailoring the dosage and/or therapeutic regimen of treatment with an agent which modulates 32616 activity.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a 32616 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a 32616 molecule or 32616 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a 32616 molecule or 32616 modulator, such as a modulator identified by one of the exemplary screening assays described herein.

This invention is further illustrated by the following examples which should not be construed as limiting. The contents of all references, patents and published patent applications cited throughout this application, as well as the Figures, are incorporated herein by reference.

IV. Recombinant Expression Vectors and Host Cells Used in the Methods of the Invention The methods of the invention (e.g., the screening assays described herein) include the use of vectors, preferably expression vectors, containing a nucleic acid encoding a 32616 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 32616 proteins, mutant forms of 32616 proteins, fusion proteins, and the like).

The recombinant expression vectors to be used in the methods of the invention can be designed for expression of 32616 proteins in prokaryotic or eukaryotic cells. For example, 32616 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 32616 activity assays, (e.g., direct assays or competitive assays described in detail below), or to generate antibodies specific for 32616 proteins. In a preferred embodiment, a 32616 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 32616 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics,* Vol. 1(1) 1986.

Another aspect of the invention pertains to the use of host cells into which a 32616 nucleic acid molecule of the invention is introduced, e.g., a 32616 nucleic acid molecule within a recombinant expression vector or a 32616 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32616 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 32616 protein. Accordingly, the invention further provides methods for producing a 32616 protein using the host cells of the invention. In one embodiment, the method comprises culturing the host cell of the invention (into which a recombinant expression vector encoding a 32616 protein has been introduced) in a suitable medium such that a 32616 protein is produced. In another embodiment, the method further comprises isolating a 32616 protein from the medium or the host cell.

V. Isolated Nucleic Acid Molecules Used in the Methods of the Invention

The cDNA sequence of the isolated human 32616 gene and the predicted amino acid sequence of the human 32616 polypeptide are shown in SEQ ID NOs:1 and 2, respectively, and in FIGS. 1A-1B.

The methods of the invention include the use of isolated nucleic acid molecules that encode 32616 proteins or biologically active portions thereof, as well as nucleic acid fragments sufficient for use as hybridization probes to identify 32616-encoding nucleic acid molecules (e.g., 32616 mRNA) and fragments for use as PCR primers for the amplification or mutation of 32616 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:1 or 3, or a portion thereof, can be isolated using standard molecular biology techniques and the sequence information provided herein. Using all or portion of the nucleic acid sequence of SEQ ID NO:1 or 3 as a hybridization probe, 32616 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 32616 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1 or 3, a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3 such that it can hybridize to the nucleotide sequence shown in SEQ ID NO:1 or 3 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence shown in SEQ ID NO:1 or 3, or a portion of any of this nucleotide sequence.

Moreover, the nucleic acid molecules used in the methods of the invention can comprise only a portion of the nucleic acid sequence of SEQ ID NO:1 or 3, for example, a fragment which can be used as a probe or primer or a fragment encoding a portion of a 32616 protein, e.g., a biologically active portion of a 32616 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3 or an anti-sense sequence of SEQ ID NO:1 or 3, or of a naturally occurring allelic variant or mutant of SEQ ID NO:1 or 3. In one embodiment, a nucleic acid molecule used in the methods of the present invention comprises a nucleotide sequence which is greater than 50, 50–100, 100–200, 200–300, 300–400, 400–500, 500–600, 600–700, 700– 800, 800–900, 900–1000, 1000–1100 or more nucleotides in length and hybridizes under stringent hybridization conditions to a nucleic acid molecule of SEQ ID NO:1 or 3.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology,* Ausubel et al., eds., John Wiley & Sons, Inc. (1995), sections 2, 4 and 6. Additional stringent conditions can be found in *Molecular Cloning: A Laboratory Manual,* Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65–70° C. (or hybridization in 4×SSC plus 50% formamide at about 42–50° C.) followed by one or more washes in 1×SSC, at about 65–70° C. A further preferred, non-limiting example of stringent hybridization conditions includes hybridization at 6×SSC at 45° C., followed by one or more washes in 0.2×SSC, 0.1% SDS at 65° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4× or 6×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°\,C.)=2(\#\text{ of A+T bases})+4(\#\text{ of G+C bases})$. For hybrids between 18 and 49 base pairs in length, $T_m(°\,C.)=81.5+16.6(\log_{10}[Na^+])+0.41(\%G+C)-(600/N)$, where N is the number of bases in the hybrid, and $[Na^+]$ is the concentration of sodium ions in the hybridization buffer ($[Na^+]$ for $1\times SSC=0.165$ M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 32616 protein, such as by measuring a level of a 32616-encoding nucleic acid in a sample of cells from a subject e.g., detecting 32616 mRNA levels or determining whether a genomic 32616 gene has been mutated or deleted.

The methods of the invention further encompass the use of nucleic acid molecules that differ from the nucleotide sequence shown in SEQ ID NO:1 or 3 due to degeneracy of the genetic code and thus encode the same 32616 proteins as those encoded by the nucleotide sequence shown in SEQ ID NO:1 or 3. In another embodiment, an isolated nucleic acid molecule included in the methods of the invention has a nucleotide sequence encoding a protein having an amino acid sequence shown in SEQ ID NO:2.

The methods of the invention further include the use of allelic variants of huma 32616, e.g., functional and non-functional allelic variants. Functional allelic variants are naturally occurring amino acid sequence variants of the huma 32616 protein that maintain a 32616 activity. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the huma 32616 protein that do not have a 32616 activity. Non-functional allelic variants will typically contain a non-conservative substitution, deletion, or insertion or premature truncation of the amino acid sequence of SEQ ID NO:2, or a substitution, insertion or deletion in critical residues or critical regions of the protein.

The methods of the present invention may further use non-human orthologues of the huma 32616 protein. Orthologues of the huma 32616 protein are proteins that are isolated from non-human organisms and possess the same 32616 activity.

The methods of the present invention further include the use of nucleic acid molecules comprising the nucleotide sequence of SEQ ID NO:1 or 3, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 32616 (e.g., the sequence of SEQ ID NO:2) without altering the biological activity, whereas an "essential" amino acid residue is required for biological activity. For example, amino acid residues that are conserved among the 32616 proteins of the present invention and other members of the short-chain dehydrogenase family are not likely to be amenable to alteration.

Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32616 protein is preferably replaced with another amino acid residue from the same side chain family. Alternatively, in another embodiment, mutations can be introduced randomly along all or part of a 32616 coding sequence, such as by saturation mutagenesis, and the resultant mutants can be screened for 32616 biological activity to identify mutants that retain activity. Following mutagenesis of SEQ ID NO:1 or 3, the encoded protein can be expressed recombinantly and the activity of the protein can be determined using an assay described herein.

Another aspect of the invention pertains to the use of isolated nucleic acid molecules which are antisense to the nucleotide sequence of SEQ ID NO:1 or 3. An "antisense" nucleic acid comprises a nucleotide sequence which is complementary to a "sense" nucleic acid encoding a protein, e.g., complementary to the coding strand of a double-stranded cDNA molecule or complementary to an mRNA sequence.

Accordingly, an antisense nucleic acid can hydrogen bond to a sense nucleic acid. The antisense nucleic acid can be complementary to an entire 32616 coding strand, or to only a portion thereof. In one embodiment, an antisense nucleic acid molecule is antisense to a "coding region" of the coding strand of a nucleotide sequence encoding a 32616. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 32616. The term "noncoding region" refers to 5' and 3' sequences which flank the coding region that are not translated into amino acids (also referred to as 5' and 3' untranslated regions).

Given the coding strand sequences encoding 32616 disclosed herein, antisense nucleic acids of the invention can be designed according to the rules of Watson and Crick base pairing. The antisense nucleic acid molecule can be complementary to the entire coding region of 32616 mRNA, but more preferably is an oligonucleotide which is antisense to only a portion of the coding or noncoding region of 32616 mRNA. For example, the antisense oligonucleotide can be complementary to the region surrounding the translation start site of 32616 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules used in the methods of the invention are typically administered to a subject or generated in situ such that they hybridize with or bind to cellular mRNA and/or genomic DNA encoding a 32616 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The anti sense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585–591)) can be used to catalytically cleave 32616 mRNA transcripts to thereby inhibit translation of 32616 mRNA. A ribozyme having specificity for a 32616-encoding nucleic acid can be designed based upon the nucleotide sequence of a 32616 cDNA disclosed herein (i.e., SEQ ID NO:1 or 3). For example, a derivative of a Tetrahymena L-19 IVS RNA can be constructed in which the nucleotide sequence of the active site is complementary to the nucleotide sequence to be cleaved in a 32616-encoding mRNA. See, e.g., Cech et al. U.S. Pat. No. 4,987,071; and Cech et al. U.S. Pat. No. 5,116,742. Alternatively, 32616 mRNA can be used to select a catalytic RNA having a specific ribonuclease activity from a pool of RNA molecules. See, e.g., Bartel, D. and Szostak, J. W. (1993) *Science* 261:1411–1418.

Alternatively, 32616 gene expression can be inhibited by targeting nucleotide sequences complementary to the regulatory region of the 32616 (e.g., the 32616 promoter and/or enhancers) to form triple helical structures that prevent transcription of the 32616 gene in target cells. See generally, Helene, C. (1991) *Anticancer Drug Des.* 6(6): 569–84; Helene, C. et al. (1992) *Ann. N. Y Acad. Sci.* 660:27–36; and Maher, L. J. (1992) *Bioessays* 14(12):807–15.

In yet another embodiment, the 32616 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. and Nielsen (1996) supra and Perry-O'Keefe et al. (1996) *Proc. Natl. Acad. Sci. USA* 93:14670–675.

PNAs of 32616 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 32616 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of 32616 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 32616 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res.* 17: 5973–88). PNA monomers are then coupled in a stepwise manner to produce a chimeric molecule with a 5' PNA segment and a 3' DNA segment (Finn et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Biotechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

VI. Isolated 32616 Proteins and Anti-32616 Antibodies Used in the Methods of the Invention The methods of the invention include the use of isolated 32616 proteins, and biologically active portions thereof, as well as polypeptide fragments suitable for use as immunogens to raise anti-32616 antibodies. In one embodiment, native 32616 proteins can be isolated from cells or tissue sources by an appropriate purification scheme using standard protein purification techniques. In another embodiment, 32616 proteins are produced by recombinant DNA techniques. Alternative to recombinant expression, a 32616 protein or polypeptide can be synthesized chemically using standard peptide synthesis techniques.

As used herein, a "biologically active portion" of a 32616 protein includes a fragment of a 32616 protein having a 32616 activity. Biologically active portions of a 32616 protein include peptides comprising amino acid sequences sufficiently identical to or derived from the amino acid sequence of the 32616 protein, e.g., the amino acid sequence shown in SEQ ID NO:2, which include fewer amino acids than the full length 32616 proteins, and exhibit at least one activity of a 32616 protein. Typically, biologically active portions comprise a domain or motif with at least one activity of the 32616 protein. A biologically active portion of a 32616 protein can be a polypeptide which is, for example, 25, 50, 75, 100, 125, 150, 175, 200, 250, 300 or more amino acids in length. Biologically active portions of a 32616 protein can be used as targets for developing agents which modulate a 32616 activity.

In a preferred embodiment, the 32616 protein used in the methods of the invention has an amino acid sequence shown in SEQ ID NO:2. In other embodiments, the 32616 protein is substantially identical to SEQ ID NO:2, and retains the functional activity of the protein of SEQ ID NO:2, yet differs in amino acid sequence due to natural allelic variation or mutagenesis, as described in detail in subsection V above. Accordingly, in another embodiment, the 32616 protein used in the methods of the invention is a protein which comprises an amino acid sequence at least about 50%, 55%, 60%, 65%, 70%, 75%, 80%, 85%, 90%, 95%, 96%, 97%, 98%, 99%, 99.1% 99.2%, 99.3%, 99.4%, 99.5%, 99.6%, 99.7%, 99.8%, 99.9% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 32616 amino acid sequence of SEQ ID NO:2 having 311 amino acid residues, at least 93, preferably at least 124, more preferably at least 156, even more preferably at least 187, and even more preferably at least 218, 249, 280 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 2.0U), using a PAM 120 weight residue table, a gap length penalty of 12 and a gap penalty of 4.

The methods of the invention may also use 32616 chimeric or fusion proteins. As used herein, a 32616 "chimeric protein" or "fusion protein" comprises a 32616 polypeptide operatively linked to a non-32616 polypeptide. A "32616 polypeptide" refers to a polypeptide having an amino acid sequence corresponding to a 32616 molecule, whereas a "non-32616 polypeptide" refers to a polypeptide having an amino acid sequence corresponding to a protein which is not substantially homologous to the 32616 protein, e.g., a protein which is different from the 32616 protein and which is derived from the same or a different organism. Within a 32616 fusion protein the 32616 polypeptide can correspond to all or a portion of a 32616 protein. In a preferred embodiment, a 32616 fusion protein comprises at least one biologically active portion of a 32616 protein. In another preferred embodiment, a 32616 fusion protein comprises at least two biologically active portions of a 32616 protein. Within the fusion protein, the term "operatively linked" is intended to indicate that the 32616 polypeptide and the non-32616 polypeptide are fused in-frame to each other. The non-32616 polypeptide can be fused to the N-terminus or C-terminus of the 32616 polypeptide.

For example, in one embodiment, the fusion protein is a GST-32616 fusion protein in which the 32616 sequences are fused to the C-terminus of the GST sequences. Such fusion proteins can facilitate the purification of recombinant 32616.

In another embodiment, this fusion protein is a 32616 protein containing a heterologous signal sequence at its N-terminus. In certain host cells (e.g., mammalian host cells), expression and/or secretion of 32616 can be increased through use of a heterologous signal sequence.

The 32616 fusion proteins used in the methods of the invention can be incorporated into pharmaceutical compositions and administered to a subject in vivo. The 32616 fusion proteins can be used to affect the bioavailability of a 32616 substrate. Use of 32616 fusion proteins may be useful therapeutically for the treatment of disorders caused by, for example, (i) aberrant modification or mutation of a gene encoding a 32616 protein; (ii) mis-regulation of the 32616 gene; and (iii) aberrant post-translational modification of a 32616 protein.

Moreover, the 32616-fusion proteins used in the methods of the invention can be used as immunogens to produce anti-32616 antibodies in a subject, to purify 32616 ligands and in screening assays to identify molecules which inhibit the interaction of 32616 with a 32616 substrate.

Preferably, a 32616 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 32616-encoding nucleic acid can be cloned into such an expression vector such that the fusion moiety is linked in-frame to the 32616 protein.

The present invention also pertains to the use of variants of the 32616 proteins which function as either 32616 agonists (mimetics) or as 32616 antagonists. Variants of the 32616 proteins can be generated by mutagenesis, e.g., discrete point mutation or truncation of a 32616 protein. An agonist of the 32616 proteins can retain substantially the same, or a subset, of the biological activities of the naturally occurring form of a 32616 protein. An antagonist of a 32616 protein can inhibit one or more of the activities of the naturally occurring form of the 32616 protein by, for example, competitively modulating a 32616-mediated activity of a 32616 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 32616 protein.

In one embodiment, variants of a 32616 protein which function as either 32616 agonists (mimetics) or as 32616 antagonists can be identified by screening combinatorial libraries of mutants, e.g., truncation mutants, of a 32616 protein for 32616 protein agonist or antagonist activity. In one embodiment, a variegated library of 32616 variants is generated by combinatorial mutagenesis at the nucleic acid level and is encoded by a variegated gene library. A variegated library of 32616 variants can be produced by, for example, enzymatically ligating a mixture of synthetic oligonucleotides into gene sequences such that a degenerate set of potential 32616 sequences is expressible as individual polypeptides, or alternatively, as a set of larger fusion proteins (e.g., for phage display) containing the set of 32616 sequences therein. There are a variety of methods which can be used to produce libraries of potential 32616 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 32616 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 32616 protein coding sequence can be used to generate a variegated population of 32616 fragments for screening and subsequent selection of variants of a 32616 protein. In one embodiment, a library of coding sequence fragments can be generated by treating a double stranded PCR fragment of a 32616 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 32616 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 32616 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 32616 variants (Arkin and Youvan (1992) Proc. Natl. Acad. Sci. USA 89:7811–7815; Delagrave et al. (1993) Prot. Eng. 6(3): 327–331).

The methods of the present invention further include the use of anti-32616 antibodies. An isolated 32616 protein, or a portion or fragment thereof, can be used as an immunogen to generate antibodies that bind 32616 using standard techniques for polyclonal and monoclonal antibody preparation. A full-length 32616 protein can be used or, alternatively, antigenic peptide fragments of 32616 can be used as immunogens. The antigenic peptide of 32616 comprises at least 8 amino acid residues of the amino acid sequence shown in SEQ ID NO:2 and encompasses an epitope of 32616 such that an antibody raised against the peptide forms a specific immune complex with the 32616 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 32616 that are located on the surface of the protein, e.g., hydrophilic regions, as well as regions with high antigenicity.

A 32616 immunogen is typically used to prepare antibodies by immunizing a suitable subject, (e.g., rabbit, goat, mouse, or other mammal) with the immunogen. An appropriate immunogenic preparation can contain, for example, recombinantly expressed 32616 protein or a chemically synthesized 32616 polypeptide. The preparation can further include an adjuvant, such as Freund's complete or incomplete adjuvant, or similar immunostimulatory agent. Immunization of a suitable subject with an immunogenic 32616 preparation induces a polyclonal anti-32616 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 32616. Examples of immunologically active portions of immunoglobulin molecules include F(ab) and F(ab')₂ fragments which can be generated by treating the antibody with an enzyme such as pepsin. The invention provides polyclonal and monoclonal antibodies that bind 32616 molecules. The term "monoclonal antibody" or "monoclonal antibody composition", as used herein, refers to a population of antibody molecules that contain only one species of an antigen binding site capable of immunoreacting with a particular epitope of 32616. A monoclonal antibody composition thus typically displays a single binding affinity for a particular 32616 protein with which it immunoreacts.

Polyclonal anti-32616 antibodies can be prepared as described above by immunizing a suitable subject with a 32616 immunogen. The anti-32616 antibody titer in the immunized subject can be monitored over time by standard techniques, such as with an enzyme linked immunosorbent assay (ELISA) using immobilized 32616. If desired, the antibody molecules directed against 32616 can be isolated from the mammal (e.g., from the blood) and further purified by well known techniques, such as protein A chromatography to obtain the IgG fraction. At an appropriate time after immunization, e.g., when the anti-32616 antibody titers are highest, antibody-producing cells can be obtained from the subject and used to prepare monoclonal antibodies by standard techniques, such as the hybridoma technique originally described by Kohler and Milstein (1975) Nature 256:495–497) (see also, Brown et al. (1981) J. Immunol. 127:539–46; Brown et al. (1980) J. Biol. Chem. 255:4980–83; Yeh et al. (1976) Proc. Natl. Acad. Sci. USA 76:2927–31; and Yeh et al. (1982) Int. J. Cancer 29:269–75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77–96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387–402; Gefter, M. L. et al. (1977) Somat. Cell Genet. 3:231–36). Briefly, an immortal cell line (typically a myeloma) is fused to lymphocytes (typically splenocytes) from a mammal immunized with a 32616 immunogen as described above, and the culture supernatants of the resulting hybridoma cells are screened to identify a hybridoma producing a monoclonal antibody that binds 32616.

Any of the many well known protocols used for fusing lymphocytes and immortalized cell lines can be applied for the purpose of generating an anti-32616 monoclonal antibody (see, e.g., G. Galfre et al. (1977) Nature 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 32616, e.g., using a standard ELISA assay.

Alternative to preparing monoclonal antibody-secreting hybridomas, a monoclonal anti-32616 antibody can be identified and isolated by screening a recombinant combinatorial immunoglobulin library (e.g., an antibody phage display library) with 32616 to thereby isolate immunoglobulin library members that bind 32616. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrard et al. (1991) *Biotechnology* (NY) 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-32616 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Cancer Res.* 47:999–1005; Wood et al. (1985) *Nature* 314: 446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

An anti-32616 antibody can be used to detect 32616 protein (e.g., in a cellular lysate or cell supernatant) in order to evaluate the abundance and pattern of expression of the 32616 protein. Anti-32616 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

VII. Electronic Apparatus Readable Media and Arrays

Electronic apparatus readable media comprising a 32616 modulator of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 32616 modulators of the present invention.

A variety of software programs and formats can be used to store the marker information of the present invention on the electronic apparatus readable medium. For example, the nucleic acid sequence corresponding to the 32616 modulators can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the 32616 modulators of the present invention.

By providing 32616 modulators of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a tumorigenic/angiogenic disorder or a pre-disposition to a tumorigenic/angiogenic disroder, wherein the method comprises the steps of determining the presence or absence of a 32616 modulator and based on the presence or absence of the 32616 modulator, determining whether the subject has a tumorigenic/angiogenic disorder or a pre-disposition to a tumorigenic/angiogenic disorder and/or recommending a particular treatment for the tumorigenic/angiogenic disorder or pre-tumorigenic/angiogenic disorder condition.

The present invention further provides in an electronic system and/or in a network, a method for determining whether a subject has a tumorigenic/angiogenic disorder or a pre-disposition to a tumorigenic/angiogenic disorder associated with a 32616 modulator wherein the method comprises the steps of determining the presence or absence of the 32616 modulator, and based on the presence or absence of the 32616 modulator, determining whether the subject has a tumorigenic/angiogenic disorder or a pre-disposition to a tumorigenic/angiogenic disorder, and/or recommending a particular treatment for the tumorigenic/angiogenic disorder or pre-tumorigenic/angiogenic disorder condition. The method may further comprise the step of receiving phenotypic information associated with the subject and/or acquiring from a network phenotypic information associated with the subject.

The present invention also provides in a network, a method for determining whether a subject has a tumorigenic/angiogenic disorder or a pre-disposition to a tumorigenic/angiogenic disorder associated with a 32616 modulator, said method comprising the steps of receiving information associated with the 32616 modulator receiving phenotypic information associated with the subject, acquiring information from the network corresponding to the 32616 modulator and/or tumorigenic/angiogenic disorder, and based on one or more of the phenotypic information, the 32616 modulator, and the acquired information, determining whether the subject has a tumorigenic/angiogenic disorder or a pre-disposition to a tumorigenic/angiogenic disorder. The method may further comprise the step of recommending a particular treatment for the tumorigenic/angiogenic disorder or pre-tumorigenic/angiogenic disorder condition.

The present invention also provides a business method for determining whether a subject has a tumorigenic/angiogenic disorder or a pre-disposition to a tumorigenic/angiogenic disorder, said method comprising the steps of receiving information associated with the 32616 modulator, receiving phenotypic information associated with the subject, acquiring information from the network corresponding to the 32616 modulator and/or tumorigenic/angiogenic disorder, and based on one or more of the phenotypic information, the 32616 modulator, and the acquired information, determining whether the subject has a tumorigenic/angiogenic disorder or a pre-disposition to a tumorigenic/angiogenic disorder. The method may further comprise the step of recommending a particular treatment for the tumorigenic/angiogenic disorder or pre-tumorigenic/angiogenic disorder condition.

The invention also includes an array comprising a 32616 modulator of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of tumorigenic/angiogenic disorder, progression of tumorigenic/angiogenic disorder, and processes, such a cellular transformation associated with tumorigenic/angiogenic disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification of 32616 as a Regulator of Tumorigenesis and/or Angiogenesis In order to determine whether the 32616 molecules are involved in tumorigenesis and/or angiogenesis, gene expression of these molecules in hemangioma endothelial cells, and various tumor tissues, such as, lung tumor, breast tumor, ovary tumor, and colon tumor was compared to gene expression in their normal counterpart cells. Regulation of 32616 expression was also examined during in vitro endothelial tube formation and in fetal tissues. Results of these experiments demonstrated that 32616 activity is upregulated in proliferating endothelial cells; in early stages of in vitro endothelial tube formation; and in various tumor and angiogenic tissues including hemangioma. In addition, 32616 is highly expressed in fetal tissues.

Figure 2B:
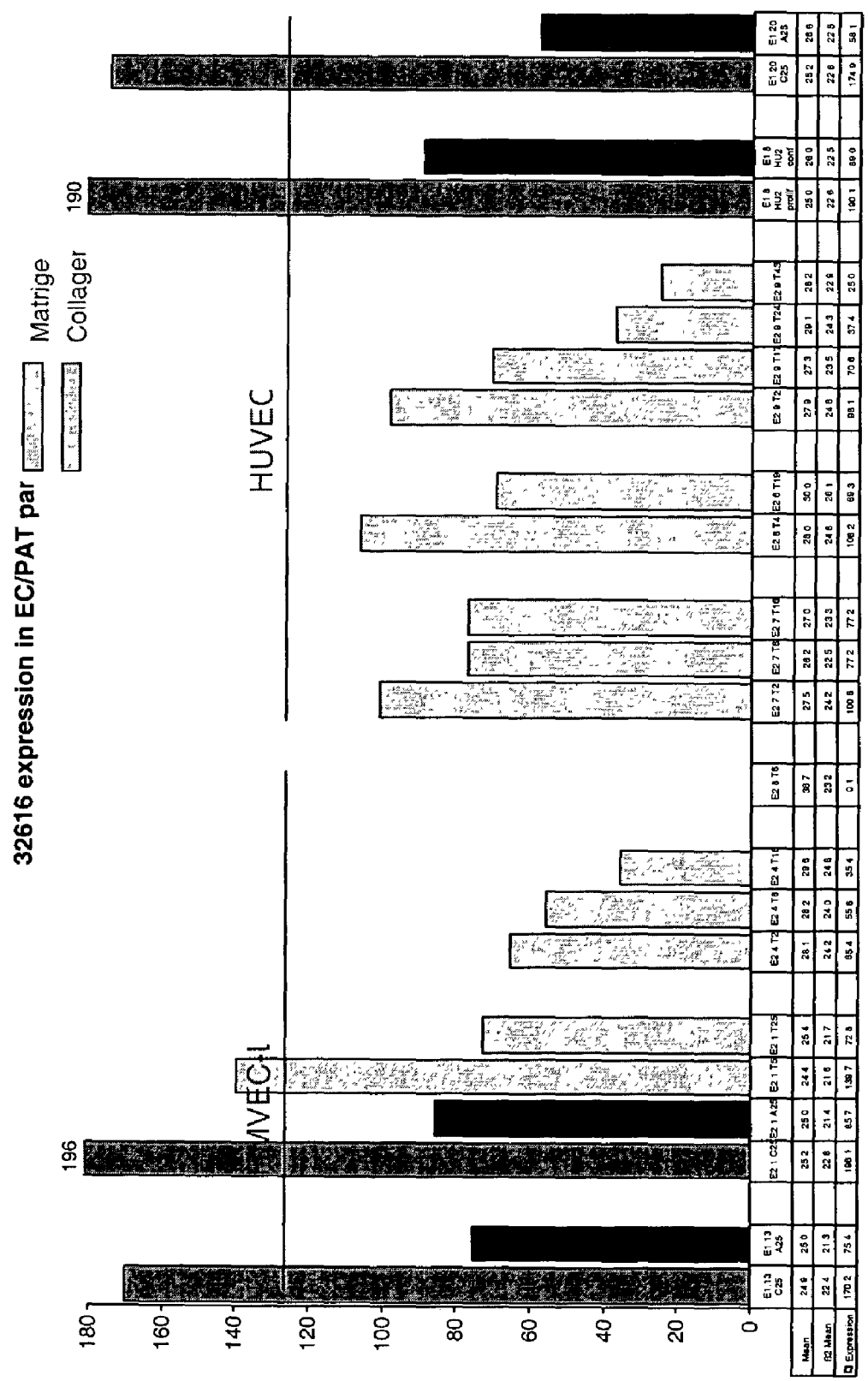
FIG. 2B is a graph showing upregulation of 32616 expression in proliferating endothelial cells cultured on a matrigel or a collagen-coated dish, as determined by Taqman™ analysis.
Figure 3:
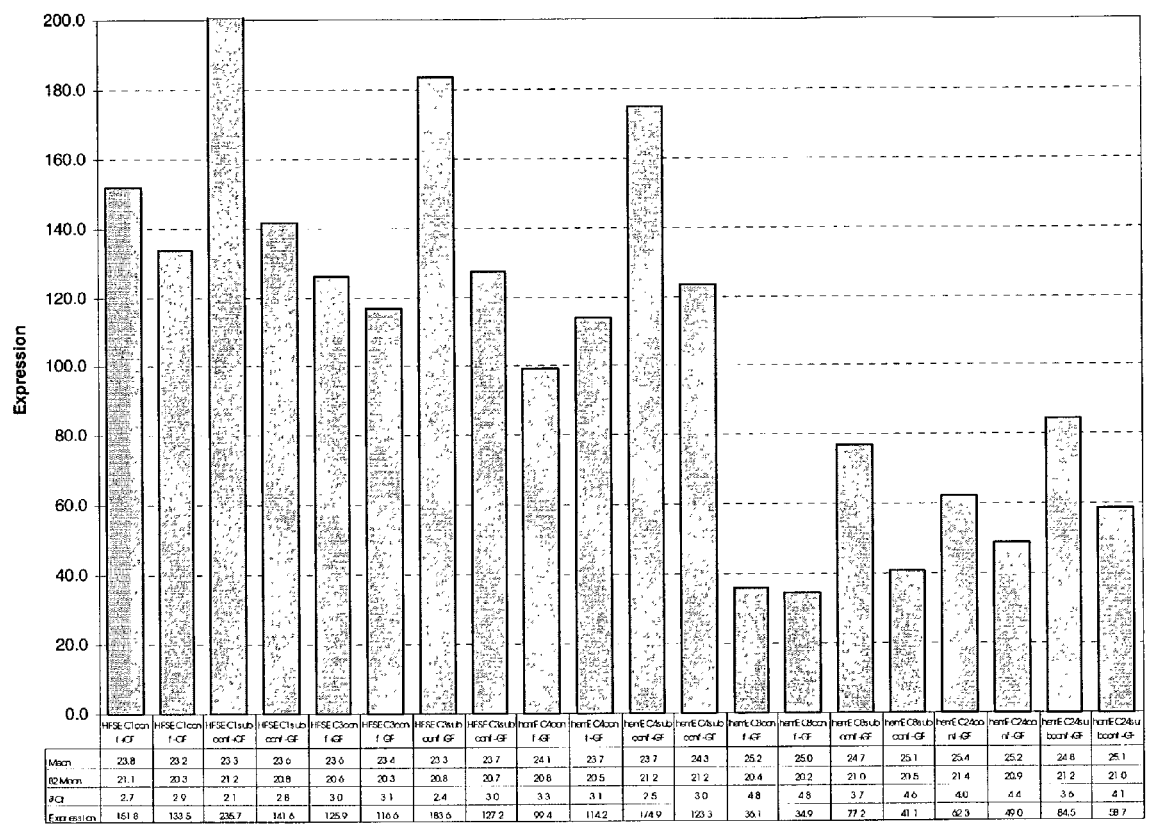
FIG. 3 is a graphical representation of 32616 expression in a hemangioma model panel. Normal and hemangioma endothelial cells, and hemangioma tissues were cultured under different growth conditions and 32616 expression were analyzed.

Distribution of Human 32616 mRNA in Proliferating Endothelial Cells as Determined by Taqman™ Analysis 32616 gene expression pattern was analyzed in the proliferating human umbilical vein endothelial (HUVEC), human microvascular endothelial cells (HMVEC-cardiac) and HMVEC-lung. Proliferating endothelial cells were drown to 70% confluence in the presence of the growth factor cocktail, whereas, arresting endothelial cells were grown to 100% confluence and the growth factor cocktail was withdrawn for 16–20 hours (see FIG. 2A). The upregulation of 32616 expression in proliferating endothelial cells was confirmed by similarly analyzing the gene expression pattern of 32616 in cells cultured in the presence of different extracellular matrix (ECM) environments, such as, matrigel or collagen (FIG. 2B).

The results indicate that 32616 is expressed at higher levels in proliferating endothelial cells as compared to control non-proliferating cells (see FIG. 2).

Up-regulation of Human 32616 mRNA in Multiple Cancers Using Taqman™ Analysis

This example describes the upregulation of human 32616 mRNA in a variety of cancers, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., tumors from lung, ovary, colon, and breast normal, hemangioma, and tumor samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Figure 4:
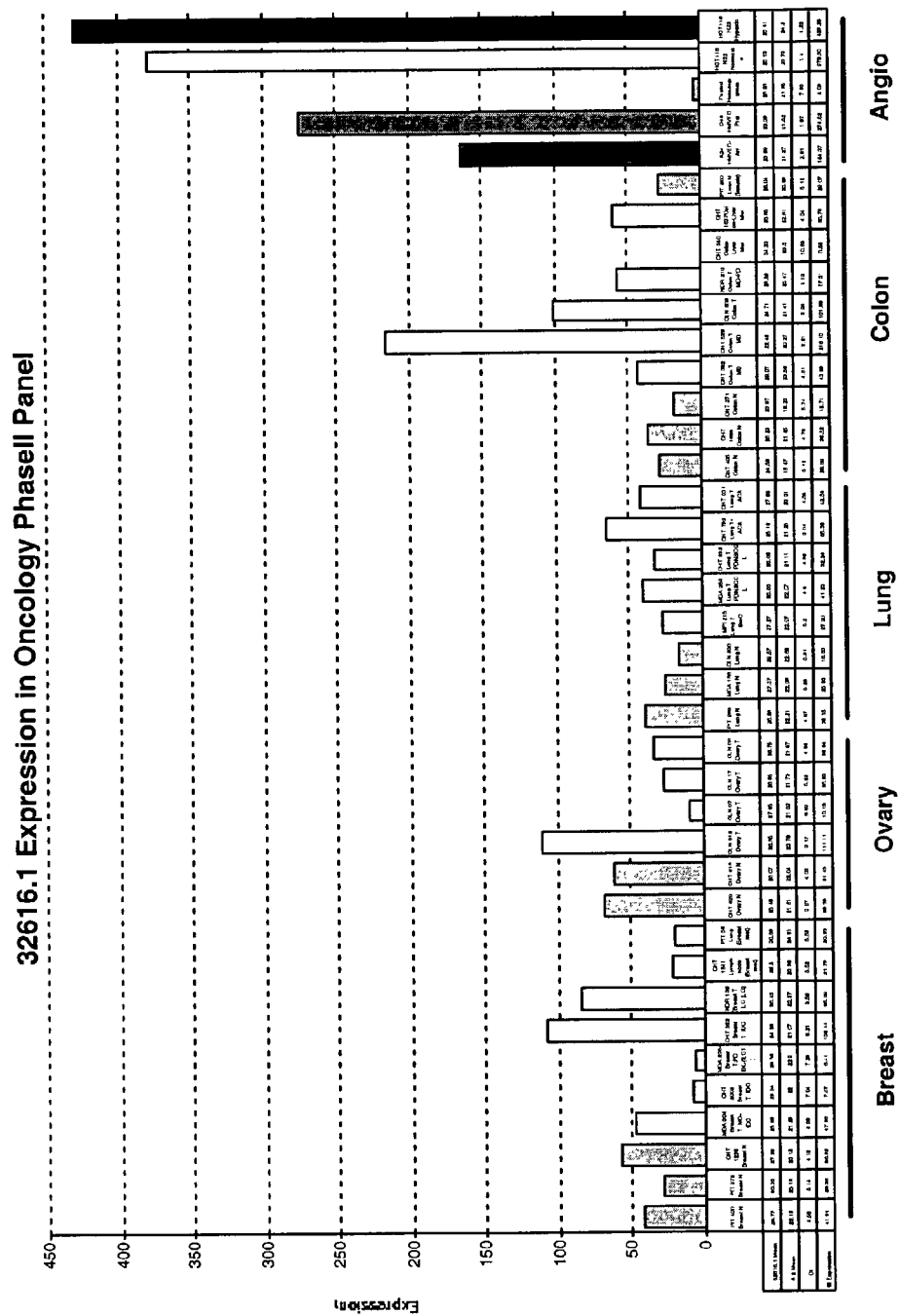
FIG. 4 is a graphical representation of 32616 expression in samples derived from multiple cancerous and angiogenic tissues, as determined by Taqman™ analysis.

These data reveal a significant up-regulation of 32616 mRNA in tumors (T), particularly breast, lung, ovary, colon tumors, and during angiogenesis, as compared to respective normal (N) tissues (see FIG. 4). Given that the mRNA for 32616 is expressed in a variety of tumors, with significant up-regulation in tumor and angiogenic samples in comparison to normal samples, it is believed that inhibition of 32616 activity may inhibit tumor progression by, for example, inhibiting tumorigenesis, angiogenesis, cellular growth and proliferation.

Expression Profile of Human 32616 mRNA in Hemangioma Endothelial Cells by Transcriptional Profiling This example describes the expression profile of 32616 mRNA, as determined by Northern blot analysis.

Northern blot hybridization with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations. Results from these experiments demonstrate a higher level of 32616 expression in proliferating hemangioma cells, thereby underscoring the possibility that inhibition of 32616 activity may inhibit angiogenic disorders (see FIGS. 3 and 5).

Tissue Distribution of Human 32616 by In situ Analysis

For in situ analysis, various tissues, e.g., tissues obtained from normal colon, breast, lung, and ovarian normal tissue, as well as colon, breast, lung, and ovarian tumors, colon metastatic to the liver, and angiogenic tissues were first frozen on dry ice. Ten-micrometer-thick sections of the tissues were post-fixed with 4% formaldehyde in DEPC treated 1×phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

In situ hybridization results indicated expression of 32616 in all tumor and angiogenic tissues, with no expression in normal tissue counterparts. Expression was detected in 3 out of 3 breast tumors, 4 out of 4 lung tumors, 4 out of 4 colon tumors (including 2 adenomas and 2 colon metastasis), and in 2 out of 2 ovary tumor tested.

Distribution of Human 32616 mRNA in Angiogenic Tissues Using Taqman™ Analysis

This example describes the distribution of human 32616 mRNA in angiogenic and fetal tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., hemangiomas, angiogenic tumor samples, and fetal tissues, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Figure 5:
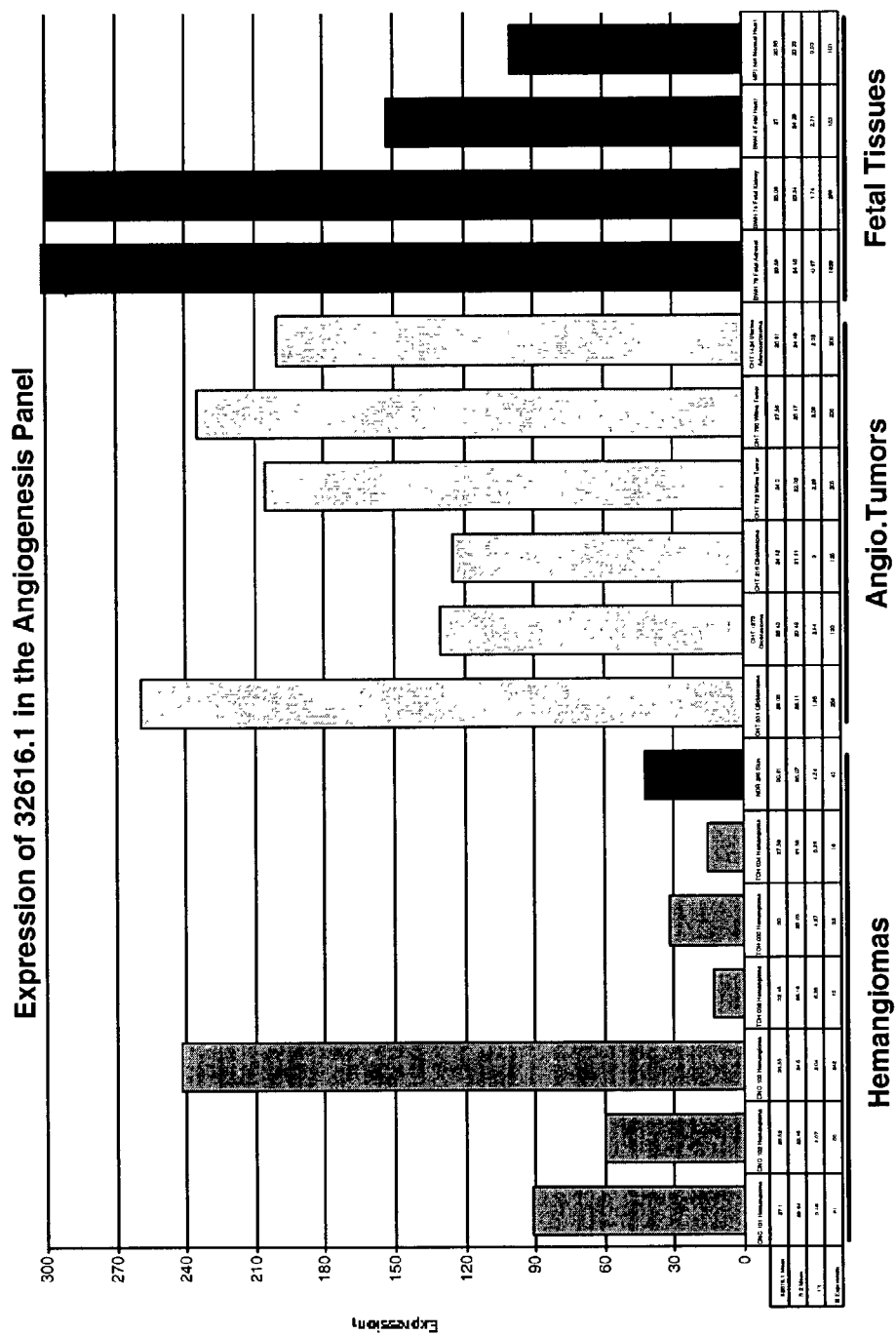
FIG. 5 is a graphical representation of 32616 mRNA expression in various angiogenic tissues, hemangioma and fetal tissues using Taqman™ analysis.

Results from these experiments reveal a significant upregulation of 32616 mRNA in hemangiomas, as compared to respective normal (N) skin tissues (see FIG. 5). Given that the mRNA for 32616 is significantly up-regulated in hemangioma samples in comparison to normal samples, it is believed that inhibition of 32616 activity may inhibit angiogenesis.

Example 2

Expression of Recombinant 32616 Polypeptide in Bacterial Cells

In this example, human 32616 is expressed as a recombinant glutathione-S-transferase (GST) fusion polypeptide in E. coli and the fusion polypeptide is isolated and characterized. Specifically, 32616 is fused to GST and this fusion polypeptide is expressed in E. coli, e.g., strain PEB199. Expression of the GST-32616 fusion polypeptide in PEB 199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant 32616 Polypeptide in cos Cells

To express the human 32616 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 32616 polypeptide and an HA tag (Wilson et al. (1984) *Cell* 37:767) or a FLAG tag fused in-frame to its 3' end of the fragment is cloned into the polylinker region of the vector, thereby placing the expression of the recombinant polypeptide under the control of the CMV promoter.

To construct the plasmid, the human 32616 DNA sequence is amplified by PCR using two primers. The 5' primer contains the restriction site of interest followed by approximately twenty nucleotides of the 32616 coding sequence starting from the initiation codon; the 3' end sequence contains complementary sequences to the other restriction site of interest, a translation stop codon, the HA tag or FLAG tag and the last 20 nucleotides of the 32616 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 32616 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the human 32616-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the IC54420 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the human 32616 coding sequence is cloned directly into the polylinker of the pcDNA/Amp vector using the appropriate restriction sites. The resulting plasmid is transfected into COS cells in the manner described above, and the expression of the 32616 polypeptide is detected by radiolabelling and immunoprecipitation using a 32616-specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a compound capable of modulating cellular proliferation comprising:
   a) contacting a test compound with a sample comprising a polypeptide selected from the group consisting of:
      i) a polypeptide which is encoded by a nucleic acid molecule comprising the nucleotide sequence of SEQ ID NO:1; and
      ii) a polypeptide comprising the amino acid sequence of SEQ ID NO:2;
   b) assaying the ability of the test compound to modulate the activity of the polypeptide;
   c) contacting a cell which expresses the polypeptide with the compound identified in b); and
   d) determining the effect of the compound on cellular proliferation;
   thereby identifying a compound capable of modulating cellular proliferation.

2. The method of claim 1, wherein the sample comprises the polypeptide or a cell expressing the polypeptide.

3. The method of claim 2, wherein the cell is an endothelial cell, a stromal cell, an epithelial cell, a cell derived from an angiogenic tissue, a cell derived from a hemangioma, a breast cell, an ovarian cell, or a colon cell.

4. The method of claim 1, wherein the cell is an endothelial cell, a stromal cell, an epithelial cell, a cell derived from an angiogenic tissue, a cell derived from a hemangioma, a breast cell, an ovarian cell, or a colon cell.

5. The method of claim 1, wherein the compound is a small molecule, a peptide, or an antibody.

6. The method of claim 1, wherein the activity is fucosidase activity.

* * * * *